United States Patent
Sevick-Muraca et al.

(10) Patent No.: US 7,054,002 B1
(45) Date of Patent: May 30, 2006

(54) CHARACTERIZATION OF LUMINESCENCE IN A SCATTERING MEDIUM

(75) Inventors: Eva M. Sevick-Muraca, College Station, TX (US); Ralf H. Mayer, McLean, VA (US); Jeffery S. Reynolds, Granger, IN (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/473,303

(22) PCT Filed: Oct. 8, 1999

(86) PCT No.: PCT/US99/23709

§ 371 (c)(1),
(2), (4) Date: May 21, 2003

(87) PCT Pub. No.: WO00/22414

PCT Pub. Date: Apr. 20, 2000

(51) Int. Cl.
G01J 3/30 (2006.01)
G01J 1/58 (2006.01)

(52) U.S. Cl. ................................ 356/317; 250/459.1
(58) Field of Classification Search ........ 356/317–318, 356/417; 250/458.1, 459.1, 461.1, 461.2; 422/82.07–82.08; 436/172
See application file for complete search history.

(56) References Cited

U.S. PATENT DOCUMENTS

| 4,245,909 A | 1/1981 | Loos .......................... 600/476 |
| 4,541,438 A | 9/1985 | Parker et al. ................ 128/664 |
| 4,641,969 A | 2/1987 | Lundberg et al. ........... 356/336 |
| 4,781,460 A | 11/1988 | Bott ............................ 600/476 |
| 4,871,251 A | 10/1989 | Preikschat et al. .......... 356/342 |
| 4,890,920 A | 1/1990 | Niziolek et al. ............ 600/476 |
| 5,022,757 A | 6/1991 | Modell ........................ 128/664 |
| 5,119,815 A | 6/1992 | Chance ........................ 128/633 |
| 5,142,372 A | 8/1992 | Alfano et al. ............... 128/664 |
| 5,164,787 A | 11/1992 | Tgushi et al. ............... 600/476 |

(Continued)

FOREIGN PATENT DOCUMENTS

EP    0 959 341 A1    11/1999

(Continued)

OTHER PUBLICATIONS

Mayer, Ralf H., et al., "Measurement of the Fluorescence Lifetime in Scattering Media by Frequency-Domain Photon Migration", Applied Optics, vol. 38, No. 22, Aug. 1, 1999, pp. 4930-4938.

(Continued)

*Primary Examiner*—Hwa (Andrew) Lee
*Assistant Examiner*—Amanda H. Merlino
(74) *Attorney, Agent, or Firm*—Baker Botts L.L.P.

(57) ABSTRACT

A system (20) of the present invention includes light source instrumentation (30) to selectively illuminate a light scattering medium including a luminophore and detection instrumentation (50) to detect multiply scattered light output from the medium in response to illumination by the light source instrumentation (30). A processor (70) is operatively coupled to the detection instrumentation (50) to determine a first optical characterization of the medium from a first multiply scattered light output of a first illumination light wavelength and a second optical characterization of the medium from a second multiply scattered light output of a second illumination light wavelength different than the first illumination light wavelength. The processor (70) is operable to calculate lifetime of the luminophore from the first optical characterization, the second optical characterization, and a multiply scattered emission of the luminophore from the medium in response to excitation.

39 Claims, 11 Drawing Sheets

U.S. PATENT DOCUMENTS

| | | | |
|---|---|---|---|
| 5,190,729 A | 3/1993 | Hauenstein et al. | |
| 5,208,651 A | 5/1993 | Buican | 356/346 |
| 5,213,105 A | 5/1993 | Gratton et al. | 128/664 |
| 5,229,839 A | 7/1993 | Hayashi et al. | 600/476 |
| 5,340,991 A | 8/1994 | Fransen et al. | 128/664 |
| 5,353,799 A | 10/1994 | Chance | 128/664 |
| 5,413,098 A | 5/1995 | Benaron | 128/663 |
| 5,416,580 A | 5/1995 | Trainer | 600/476 |
| 5,421,337 A | 6/1995 | Richards-Kortum et al. | 128/633 |
| 5,421,339 A | 6/1995 | Ramanujam et al. | 128/665 |
| 5,424,843 A | 6/1995 | Tromberg et al. | 356/442 |
| 5,438,408 A | 8/1995 | Weichert et al. | 600/476 |
| 5,441,054 A | 8/1995 | Tsuchiya | 128/665 |
| 5,452,723 A | 9/1995 | Wu et al. | 128/665 |
| 5,455,675 A | 10/1995 | Witt et al. | 600/476 |
| 5,485,530 A | 1/1996 | Lakowicz et al. | 382/191 |
| 5,502,561 A | 3/1996 | Hutchins et al. | 600/476 |
| 5,504,337 A | 4/1996 | Lakowicz et al. | 250/461.2 |
| 5,507,287 A | 4/1996 | Palcic et al. | 128/633 |
| 5,579,773 A | 12/1996 | Vo-Dinh et al. | 128/665 |
| 5,582,168 A | 12/1996 | Samuels et al. | 128/633 |
| 5,590,660 A | 1/1997 | MacAulay | 128/664 |
| 5,619,324 A | 4/1997 | Harvill et al. | 356/336 |
| 5,624,847 A | 4/1997 | Lakowicz et al. | |
| 5,628,310 A | 5/1997 | Rao et al. | 600/317 |
| 5,647,368 A | 7/1997 | Zeng et al. | 128/665 |
| 5,692,504 A | 12/1997 | Essenpreis et al. | 600/316 |
| 5,699,798 A | 12/1997 | Hochman et al. | 600/420 |
| 5,736,410 A | 4/1998 | Zarling et al. | |
| 5,759,767 A | 6/1998 | Lakowicz et al. | 435/4 |
| 5,792,049 A | 8/1998 | Eppstein et al. | 600/306 |
| 5,818,583 A | 10/1998 | Sevick-Muraca et al. | |
| 5,860,421 A | 1/1999 | Eppstein et al. | 128/660.06 |
| 5,865,754 A | 2/1999 | Sevick-Muraca et al. | 600/476 |
| 5,891,656 A | 4/1999 | Zarling et al. | 435/7.92 |
| 5,917,190 A | 6/1999 | Yodh et al. | 250/458.1 |
| 5,949,077 A | 9/1999 | Alfano et al. | 250/459.1 |
| 6,216,540 B1 | 4/2001 | Nelson et al. | 73/633 |
| 6,271,522 B1 | 8/2001 | Lindermeir et al. | 250/341.1 |
| 6,480,276 B1 | 11/2002 | Jiang | 356/336 |
| 2002/0072677 A1 | 6/2002 | Sevick-Muraca et al. | |
| 2003/0117622 A1 | 6/2003 | Sevick-Muraca et al. | |
| 2005/0073681 A1 | 4/2005 | Sevick-Muraca et al. | |

FOREIGN PATENT DOCUMENTS

| | | |
|---|---|---|
| GB | 2311366 A | 3/1996 |
| JP | 2-268256 | 1/1990 |
| WO | WO 95/12132 | 5/1995 |
| WO | WO 99/49312 | 3/1999 |
| WO | WO 00/22414 | 10/1999 |
| WO | WO 02/41760 A2 | 5/2000 |
| WO | WO 01/22063 A1 | 9/2000 |

OTHER PUBLICATIONS

Cerussi, Albert E., et al., "Experimental Verification of a Theory for the Time-Resolved Fluorescence Spectroscopy of Thick Tissues", Applied Optics, vol. 36, No. 1, Jan. 1, 1997, pp. 116-124.

Hutchinson, Christina L., et al., "Fluorescence-Lifetime Determination in Tissues or Other Scattering Media from Measurement of Excitation and Emission Kinetics", Applied Optics, vol. 35, No. 13, May 1, 1996, pp. 2325-2332.

M.A. O'Leary, E.A. Boas, X.D. Li, B. Chance, and A.G. Yodh., "Fluorescence Lifetime Imaging in Turbid Media," Optics Letters, vol. 21, No. 2, pp. 158-160, Jan. 15, 1966.

Sevick-Muraca, et al.; "*Method and System for Detecting Sentinel Lymph Nodes*;" U.S. Appl. No. 10/618,194; 28 pgs, Jul. 11, 2003.

Sevick-Muraca, et al.; "*Method for Characterizing Particles in Suspension from Frequency Domain Phton Migration Measurements*" U.S. Appl. No. 10/115,271; 59 pgs, Apr. 3, 2002.

Dilip Paithankar, Jeff Kao, and Eva Sevick-Muraca, *Particle Size Distribution Estimation Via Solution of the Inverse Problem of Multi-Wavelength Scattering Coefficient Measurements*, Chem. Eng. Prog., Aug. 1995.

Sevick-Muraca, et al.; *Method for Characterizing Particles in Suspension from Frequency Domain Photon Migration Measurements*; U.S. Appl. No. 11/204,844; 59 pgs, Aug. 16, 2005.

Robert J. Farrell and Yen-Cheng Tsai, *Nonlinear Controller for Batch Crystallization: Development and Experimental Demonstration*, AIChE Journal, vol. 41, No. 10, at 2318, Oct. 1995.

Huabei Jiang, Keith D. Paulsen, Ulf L. Osterberg, Brian W. Pogue and Michael S. Patterson, *Optical Image Reconstruction Using Frequency-Domain Data: Simulations and Experiments*, Journal of the Optical Society of America, at 253, Sep. 1995.

Alwin Kienle, Lothar Lilge, Michel S. Patterson, Raimund Hibst, Rudolf Steiner, and Brian C. Wilson, *Spatially Resolved Absolute Diffuse Reflectance Measurements for Noninvasive Determination of the Optical Scattering and Absorption Coefficients of Biological Tissue*, Applied Optics, vol. 35, No. 13 at 2304, May 1996.

Pi-Huan Wang, Geoffrey S. Kent, M. Patrick McCormick, Larry W. Thomason, and Glenn K. Yue, *Retrieval Analysis of Aerosol-Size Distribution with Simulated Extinction Measurements at SAGE III Wavelenghts*, Applied Optics, vol. 35, No. 3 at 433, Jan. 1996.

Kusiel S. Shifrin and Ilja G. Zolotov, *Spectral Attenuation and Aerosol Particle Size Distribution*, Applied Optics, vol. 35, No. 12 at 2114, Apr. 1996.

Jianhong Wang and F. Ross Hallett, *Spherical Particle Size Determination by Analytical Inversion of the UV-Visible-NIR Extinction Spectrum*, Applied Optics, vol. 35, No. 1, at 193, Jan. 1996.

Sergei A. Vinogradov, Leu-Wei Lo, William T. Jenkins, Sydney M. Evans, Cameron Koch, and David F. Wilson, *Noninvasive Imaging of the Distribution in Oxygen in Tissue in Vivo Using Near-Infrared Phosphors*, Biophysical Journal, vol. 70, at 1609-1617, Apr. 1996.

Joshua B. Fishkin, Peter T.C. So, Albert E. Cerussi, Sergio Fantini, Maria Angela Franceschini, and Enrico Gratton, *Frequency-Domain Method for Measuring Spectral Properties in Multiple-Scattering Media: Methemoglobin Absorption Spectrum in a Tissuelike Phantom*, Applied Optics, vol. 34 No. 7, at 1143, Mar. 1995.

Heimo Schnablegger and Otto Glatter, *Sizing of Colloidal Particles with Light Scattering: Corrections for Beginning Multiple Scattering*, Applied Optics, vol. 34, No. 18, at 3489, Jun. 1995.

M.A. O'Leary, D.A. Boas, B. Chance, and A.G. Yodh, *Experimental Images of Heterogeneous Turbid Media by Frequency-Domain Diffusing-Photon Tomography*, Optics Letters, vol. 20, No. 5, at 426, Mar. 1995.

Jozef Vavra, Jozef Antalik and Marek Liska, *Application of Regression Analysis in Spectroturbidity Size-Characterization Methods*, Part. Syst. Charact. 12, 38-41, 1995.

Reynolds, et al., "*Imaging of Spontaneous Canine Mammary Tumors Using Fluorescent Contrast Agents*", Photochemistry and Photobiology, 1999: 70(1): 87-94 (XP-001063376), Apr. 14, 1999.

Gurfinkel, et al., "*Pharmocokinetcs of ICG and HPPH-car for the Detection of Normal and Tumor Tissue Using Fluorescence, Near-infrared Reflectance Imaging: A Case Study*", Photochemistry and Photobiology, 2000: 72(1): 94-102 (XP-001030699), Apr. 28, 2000.

Thompson, et al., "*Near-infrared fluorescence contrast-enhanced imaging with intensified charge-coupled device homodyne detection: measurement precision and accuracy*", Journal of Biomedical Optics, 2003: 8(1): 111-120 (XP-002301882)klj, Jan. 2003.

Thompson, et al., "*Near-infrared fluorescence contrast-enhanced imaging with area illumination and area detection: the forward imaging problem*", Applied Optics, 2003: 42(19): 4125-4136 (XP-002301883), Jul. 1, 2003.

Notification of Transmital of the International Search Report and the Written Opinion of the International Searching Authority for International Application No. PCT/US2004/019792, filed Jun. 18, 2004 (14 pages), Nov. 8, 2004.

Houston, et al., "*Sensitivity and Depth Penetration of Continuous Wave Versus Frequency-domain Photon Migration Near-infrared Fluorecence Contrast-enhancing Imaging*," Photochemistry and Photobiology, 2003, vol. 77(4), pp. 420-430.

Ntziachristos, et al. "*In Vivo Tomographic Imaging of Near-Infrared Fluorescent Probes*," Molecular Imaging, vol. 1(2), pp. 82-88, Apr. 2002.

Gratton, et al., *A Continuously Variable Frequency Cross-Correlation Phase Fluorometer with Picosecond Resolution*, © Biophysical Society, Biophysical Journal, vol. 44, pp. 315-324, Dec. 1983.

Gratton, et al., *The possibility of a near-infrared optical imaging system using frequency domain methods*, Mind Brain Imaging Program, Hamamatsu, Japan, pp. 183-189, Aug. 5-Oct. 1990.

Sevick, et al., *Quantitation of Time-and Frequency-Resolved Optical Spectra for the Determination of Tissue Oxygenation*, Analytical Biochemistry 195, © 1991 Academic Press Inc., pp. 330-351.

Fishkin, et al., *Propagation of photon-density waves in strongly scattering media containing an absorbing semi-infinite plane bounded by a straight edge*, vol. 10, No. 1, © 1993 Optical Society of America, pp. 127-140, Jan. 1993.

Tromberg, et al., *Properties of photon density waves in multiple-scattering media*, vol. 32, No. 4, Applied Optics, pp. 607-616, Feb. 1, 1993.

Madsen, et al., *Determination of the optical properties of the human uterus using frequency-domain photon migration and steady-state techniques*, Phys. Med. Biol. 39, © 1994 IOP Publishing Ltd., pp. 1191-1202.

Fantini, et al., *Quantitative determination of the absorption spectra of chromophores in strongly scattering media: a light-emitting-diode based technique*, Applied Optics, vol. 33, No. 22, pp. 5204-5213, Aug. 1, 1994.

Fishkin, et al., *Frequency-domain method for measuring spectral properties in multiple-scattering media: methemoglobin absorption spectrum in a tissuelike phantom*, Applied Optics, vol. 34, No. 7, pp. 1143-1155, Mar. 1, 1995.

Tromberg, et al., *Non-invasive measurements of breast tissue optical properties using frequency-domain photon migration*, Phil. Trans. R. Soc. Lond. B, © 1997 The Royal Society, pp. 661-668.

Muzzio, et al., *Sampling practices in powder blending*, Research papers, International Journal of Pharmaceutics 155, © 1997 Elsevier Science B.V., pp. 153-178.

Fishkin, et al., *Frequency-domain photon migration measurements of normal and malignant tissue optical properties in a human subject*, Applied Optics, vol. 36, No. 1, pp. 10-20, Jan. 1, 1997.

Sevick-Muraca, et al., *Photon-Migration Measurement of Latex Size Distribution in Concentrated Suspensions*, Particle Technology and Fluidization, AIChE Journal, vol. 43, No. 3, pp. 655-664, Mar. 1997.

Richter, et al., *Particle Sizing Using Frequency Domain Photon Migration*, Part. Part. Syst. Charact. 15, © Wiley-VCH Verlag GmbH, D-69469 Weinheim, pp. 9-15, 1998.

Ramanujam, et al., *Sources of phase noise in homodyne and heterodyne phase modulation devices used for tissue oximetry studies*, Review of Scientific Instruments, vol. 69, No. 8, © 1998 American Institute of Physics, pp. 3042-3054, Aug. 1998.

Chance, et al., Review Article, *Phase measurement of light absorption and scatter in human tissue*, Review of Scientific Instruments, vol. 69, No. 10, © 1998 American Institute of Physics, pp. 3457-3481, Oct. 1998.

Banerjee, et al., *Probing Static Structure of Colloid-Polymer Suspensions with Multiply Scattered Light*, Journal of Colloid and Interface Science 209, © 1999 by Academic Press, pp. 142-153.

Shinde, et al., *Investigation of static structure factor in dense suspensions by use of multiply scattered light*, Applied Optics, vol. 38, No. 1, © 1999 Optical Society of America, pp. 197-204, Jan. 1, 1999.

Gerken, et al., *High-precision-frequency-domain measurements of the optical properties of turbid media*, Optics Letters, vol. 24, No. 14, © 1999 Optical Society of America, pp. 930-932, Jul. 15, 1999.

Shinde, et al., *Frequency-Domain Photon Migration Measurements for Quantitative Assessment of Powder Absorbance: A Novel Sensor of Blend Homogeneity*, Research Articles, © 1999 American Chemical Society and American Pharmaceutical Association, Journal of Pharmaceutical Sciences, vol. 88, No. 10, pp. 959-966, Oct. 1999.

Banerjee, et al., *Assessment, of S(0, Ø) from multiply scattered light*, Journal of Chemical Physics, vol. 111, No. 20, © 1999 American Institute of Physics, pp. 9133-9136, Nov. 22, 1999.

Richter, et al., *Characterization of concentrated colloidal suspensions using time-dependent photon migration measurements*, Reprinted from Colloids And Surfaces An International Journal, A: Physciochemical and Engineering Aspects, © 2000 Elsevier Science B.V., pp. 163-173, plus cover.

Pham, et al., *Broad bandwidth frequency domain instrument for quantitive tissue optical spectroscopy*, Review of Scientific Instruments, vol. 71, No. 6, © 2000 American Institute of Physics, pp. 2500-2513, Jun. 2000.

Hawrysz, et al., *Developments Toward Diagnostic Breast Cancer Imaging Using Near-Infrared Optical Measurements and Fluorescent Contrast Agents*[1], Review Article, Neoplasia, vol. 2, No. 5, © 2000 Nature America, Inc., pp. 388-417, Sep.-Oct. 2000.

Pan, et al., *Volume of Pharmaceutical Probed by Frequency-Domain Photon Migration Measurements of Multiply Scattered Light*, Analytical Chemistry 2002, vol. 74, No. 16, © 2002 American Chemical Society, pp. 4228-4234, Aug. 15, 2002.

Sun, et al., "*Particle Characterization of Colloidal Suspension at High Volume Fractions Using Frequency Domain Photon Migration*," 6th World Congress of Chemical Engineering, Melbourne 2001, pp. 4/15-12/15.

Sun, et al., "*Inversion Algorithms for Particle Sizing with Photon Migration Measurements*," Fluid Mechanics and Transport Phenomena, AIChE Journal, vol. 47, No. 7, pp. 1487-1498, Jul. 2001.

Sun, et al., "*Approach for Particle Sizing in Dense Polydisperse Colloidal Suspension Using Multiple Scattered Light*," XP-001126299, Langmuir 2001, 17, 2001 American Chemical Society, pp. 6142-6147, Sep. 8, 2001.

Isayev, K, et al., "*Study of Thermophysical Properties of a Metal-Hydrogen System*," International Journal of Hydrogen Energy, vol. 21, No. 11-12, Nov. 12, 1996, pp. 1129-1132, Dec. 12, 1996.

Panda, et al., "*Generalized B-Spline Signal Processing*," European Journal to the Methods and Applications of Signal Processing, Elsevier Science Publishers, B.V. Amsterdam, NL, vol. 55, No. 1, Nov. 1, 1996 XP004016005, pp. 1-14.

PCT invitation to Pay Additional Fees (PCT Article 17(3)(a) and Rule 40.1), Annex to Form PCT/ISA/206 Communication Regarding to the Results of the Partial International Search Authority, regarding PCT/US02/10433, Applicant's reference 017575.0748, 6 pages, Nov. 29, 2002.

PCT International Search Report in International Application No. 02/10433, dated Jun. 16, 2003, 10 pages.

Nai-ning Wang, Gang Zheng, and Xiao-shu Cai, *A Theoretical and Experimental Study of the Total Light Scattering Technique for Particle Size Analysis*, Part. Part. Syst. Charact. 11, Feb. 1994, at 309-314.

John Dimitratos, Guillermo Elicabe, and Christos Geogakis, *Control of Emulsion Polymerization Reactors*, AIChE Journal, Dec. 1994, vol. 40, No. 12, at 1993.

Ronald G. Sparks and Charles L. Dobbs, *The Use of Laser Backscatter Instrumentation for the On-Line Measurement of the Particle Size Distribution of Emulsions*, Part. Part. Syst. Charact. 10, Jul. 1993, at 279-289.

James R. Rawlings, Stephen M. Miller, and Walter R. Witkowski, *Model Identification and Control of Solution Crystallization Process: A Review*, Ind. Eng. Chem. Res. 1993, vol. 32, No. 7, at 1276.

D. Jeffrey Lischer and Michel Y. Louge, *Optical Fiber Measurements of Particle Concentration in Dense Suspensions: Calibration and Simulation*, Applied Optics, Aug. 1992, vol. 31, No. 24, at 5106.

R. Graaff, J.G. Aarnoudse, Jr. Zijp, P.M.A. Sloot, F.F.M. Mul, J. Greve, and M.H. Koelink, *Reduced Light-Scattering Properties for Mixtures of Spherical Properties: A Simple Approximation Derived from Mie Calculations*, Applied Optics, Apr. 1992, vol. 31, No. 10 at 1370.

L. H. Garcia-Rubio, *Refractive Index Effects on the Absorption Spectra of Macromolecules*, Macromolecules, 1992, at 2608.

Guillermo E. Elicabe and Luis H. Garcia-Rubio, *Latex Particle Size Distribution from Turbidimetric Measurements*, Polymer Characterization, 1990, at 84.

J. Jager, H.J.M. Kramer, E.J. De Jong, *On-Line Particle Size Measurement in Denise Slurries*, Powder Technology, 1990. at 155-162.

Seth Fraden and Georg Maret, *Multiple Light Scattering from Concentrated, Interacting Suspensions*, Physical Review Letters, Jul. 1990, vol. 65, No. 4, at 512.

John C. Thomas and Victoria Dimonie, *Fiber Optic Dynamic Light Scattering from Concentrated Dispersion, 3: Particle Sizing in Concentrates*, Applied Optics, Dec. 1990, vol. 29, No. 36, at 5332.

Joseph Pierce, Dilip Paithankar, Christina Hutchinson, David Taylor and Eva Sevick-Muraca, *Particle Size Measurement in Suspensions through Frequency-Domain Photon Migration Measurements*, Presentation to Fine Particle Society Meeting of Aug. 25, 1995.

Michael S. Patterson, Steen J. Madsen, J. David Moulton and Brian C. Wilson, *Diffusion Equation Representation of Photon Migration in Tissue* (date unknown.).

Akira Ishimaru, Robert J. Marks, II, Leung Tsang, Chi M. Lam, Doug C. Park, *Optical Sensing of Particle Size Distribution by Neural Network Technique* (date unknown).

Eva M. Sevick-Muraca and Kavi Sharma, Measurements of Photon Migration for Particle Sizing in Optically Dense Suspensions, AIChE Journal, Nov. 1994.

Eva M. Sevick-Muraca and Dilip Paithankar, *Process Monitoring: Photon Migration Measurements in Particulate Systems*, Fine Particle Society Meeting, Aug., 1995.

Richard Haskel et al., "*Boundary conditions for the diffusion equation in radiative transfer*", J. Opt. Soc. Am., A. vol. 11, No. 10. Oct. 1994, pp. 2727-2741.

X. D. Li et al., "*Fluorescent diffuse photon density waves in homogenous and heterogeneous turbid media: analytic solutions and applications*", Applied Optics, vol. 35, No. 19, Jul. 1996, pp. 3746-3758.

Michael Patterson et al., "*Applications of time-resolved light scattering measurements to photodynamictherapy dosimetry*", Applied Optics 1203-1208.

B. W. Pogue et al., "*Initial Assessment of a simple system for frequency domain diffuse optical tomography*", Phys. Med. Biol. 40, (1995) 1709-1729.

Michael S. Patterson et al., "*Mathematical model for time-resolved and frequency-domain fluorescence spectroscopy in biological tissues*", Applied Optics, vol. 33, No. 10, Apr. 1994, pp. 1963-1974.

Jun Wu et al., "*Three-dimensional imaging of objects embedded in turbid media with fluorescence and raman spectroscopy*", Applied Optics, vol. 34, No. 18, Jun. 1995 pp. 3425-3430.

Scott R. Fulton, et al., "*Time-resolved laser-induced fluorescence spectroscopy for enhanced demarcation of human atherosclerotic plaques*", Journal of Photochemistry and Photobiology, (1990) pp. 363-369.

Seth Fraden et al., "*Multiple light scattering from concentrated, interacting suspensions*", Physical Review letters, vol. 65, No. 4, pp. 512-515.

K. M. Yoo et al., "*Imaging objects hidden in scattering media using a fluorescence-absorption technique*", Optics Letters, vol. 16, No. 16, 1991, pp. 1252-1254.

R. C. Straight et al., "*Application of Charge-coupled device technology for measurement of laser light and fluorescence distribution in tumors for photodynamic therapy*", Photochemistry and Photobiology, vol. 53, No. 6, pp. 787-796.

E. M. Sevick et al., "*Frequency domain imaging absorbers obscured by scattering*", J. Photochem, Photobiol. B:Biol, 16 (1992) pp. 169-185.

Wai S. Poon et al., "*Laser-induced Fluorescence: Experimental intraoperative delineation of tumor resection margins*", J. Neurosurg, vol. 76, Apr. 1992, pp. 679-686.

Brian C. Wilson et al., "*Time-dependent optical spectroscopy and imaging for biomedical applications*", Proceedings of the IEEE, vol. 80, No. 6, Jun. 1992 pp. 918-930.

A. Knuittel et al., "*Acoust-optic scanning and interfering photon density waves for precise localization of an absorb-*

*ing (or fluorescence) body in a turbid medium*", Rev. Sci. Instrum. vol. 64, No. 3, Mar. 1993, pp. 638-644.

R. Cubeddu et al., "*Time-gated Fluorescence imaging for the diagnosis of tumors in a murine model*", Photochemistry and Photobiology, vol. 57, No. 3, pp. 480-485.

Randall Barbour et al., "*A perturbation approach for optical diffusion tomography using continuous-wave and time-resolved data*", Medical Optical Tomography, pp. 87-121.

M. A. O'Leary et al., "*Reradiation and imaging of diffuse photon density waves using fluorescent inhomogeneities*", Journal of Luminescence, (1994) pp. 281-286.

Michael S. Patterson et al., "*Mathematical model for time-resolved and frequency-domain fluorescence spectroscopy in biological tissues*", Aplied Optics, vol. 33, No. 10, Apr. 1994, pp. 1963-1974.

David A. Russel et al., "*Continuous noninvasive measurement of In Vivo pH in conscious mice*", Photochemistry and Photobiology, vol. 59, No. 3 (1994) pp. 309-313.

Serge Mordon et al., "*In Vivo pH measurement and imaging of tumor tissue using a pH-sensitive fluorescent probe (5,6-carboxyfluorescein): Instrumental and Experimental studies*", Photochemistry and Photobiology, vol. 60, No. 3, pp. 274-279.

Jun Wu et al., "*Time-resolved multichannel imaging of fluorescent objects embedded in turbid media*", Optic Letters, vol. 20, No. 5, Mar. 1995 pp. 489-491.

CHARACTERIZATION OF LUMINESCENCE IN A SCATTERING MEDIUM

GOVERNMENT RIGHTS

The U.S. government has a paid-up license in this invention and the right in limited circumstances to require the patent owner to license others on reasonable terms as provided by the terms of the National Institute of Health grants R01CA67176-01 and K04CA68374-01.

CROSS-REFERENCE TO RELATED APPLICATIONS

The present application claims the benefit of U.S. Provisional Patent Application No. 60/103,609 to Sevick-Muraca et al. entitled "Techniques to Characterize Fluorescence Lifetime in Scattering Media" and filed 9 Oct. 1999; and is related to pending U.S. patent application to Sevick-Muraca et al. entitled "Imaging of Light Scattering Tissues with Fluorescent Contrast Agents" and filed 22 Nov. 1999 as a national stage application of International Application Number PCT/US98/02354 (U.S. patent application Ser. No. 09/367,148), all of which are hereby incorporated by reference.

BACKGROUND

The present invention relates to spectroscopic techniques involving luminescence, and more particularly, but not exclusively relates to the determination of lifetime of a luminophore in a light scattering medium.

There has been significant development of fluorescent and phosphorescent dyes or probes with decay kinetics dependent upon the presence or concentration of an analyte or metabolite. Accordingly, lifetime of these dyes can be measured to detect corresponding analyte(s) and/or metabolite(s) concentration. Fluorescent probes in the near-infrared range appear particularly promising for in vivo biomedical diagnostic techniques that involve external, non-invasive measurements or minimally invasive, endoscopic measurements of emitted light.

Unfortunately, quantitative lifetime measurements for such probes are often difficult to obtain in the light scattering environment typically encountered with in vivo diagnostics. Light scattering also hampers other applications of luminophore probes both inside and outside the biomedical field. Consequently, lifetime measurements are usually restricted to dilute, nonscattering solutions. Notably, even equipment used in this manner, such as a curvette to contain the dilute solution, tends to scatter light to some degree introducing an attendant inaccuracy.

Moreover, current lifetime measurement approaches have other limits—especially for fluorophore probes. For example, deconvolution of instrument function often hampers accurate time-domain measurement of lifetimes. In another example, frequency-domain approaches generally require a reference fluorophore with known lifetime characteristics in the environment of interest and at the appropriate excitation and emission wavelengths. Thus, there is a need for further contributions that address these limits and/or other drawbacks confronting this technology.

SUMMARY OF INVENTION

Accordingly, one form of the present invention is a unique technique to evaluate a medium including a luminophore. Other forms include unique systems and methods to measure optical properties of a luminophore in a light scattering medium.

In another form, a light scattering medium includes a luminiphore that is exposed to a number of different wavelengths. Multiply scattered light from exposure to these wavelengths is measured, and one or more optical characteristics of the medium are determined relative to the different wavelengths.

In still another form, an optical characteristic of a luminophore in a light scattering medium is determined. For this form, the medium is illuminated by light at a first wavelength corresponding to an emission wavelength of the luminophore and at a second wavelength corresponding to an excitation wavelength of the luminophore. Multiply scattered light in response to illumination by the different wavelengths is detected to optically characterize the medium and/or luminophore.

A further form of the present invention is a technique to determine the lifetime of a fluorophore. This technique includes both a method and instrumentation directed to fluorescence lifetime measurements. Preferably, this technique does not utilize a reference fluorophore and is not adversely impacted by any light scattering and absorption that might occur in a scattering medium.

Still a further form of the present invention includes a frequency-domain approach to measuring fluorescence lifetime of one or more fluorophores. This approach may include exciting a fluorophore in a light scattering sample with a modulated excitation light and detecting phase shift information. The fluorescence lifetime may be determined from the phase shift information through relationships characterizing light scattering by the sample.

In yet a further form, a light scattering sample containing a fluorophore is exposed to an intensity modulated light at a first wavelength selected to cause the fluorophore to fluoresce at a second wavelength of light. Scattered light at the first wavelength is detected and scattered light at the second wavelength is detected. Optical properties are determined from the detected scattered light to provide fluorescence lifetime based on relationships that characterize photon migration in a light scattering medium. This form may include characterizing the detected scattered light in terms of phase shift in the frequency domain.

In an additional form, a system of the present invention includes an intensity modulated excitation light source configured to deliver an excitation light of a first wavelength to a light scattering substance containing a fluorophore of interest. The fluorophore responds to the excitation light to provide a light emission at a second wavelength. Scattered light is detected at two locations spaced apart from one another. A processor gathers information corresponding to the detected scattered light and processes this information to determine fluorescence lifetime by applying relationships that characterize photon migration of scattered light. For this form, a first detector may be used for detection of light at a first one of the locations that includes a first optical fiber coupled to a first sensor. Also a second detector may be used for detection of light at a second one of the locations that includes a second optical fiber coupled to a second sensor. The first and second detectors may also include corresponding first and second optical filters to selectively detect the first wavelength of light with the first sensor and the second wavelength of light with the second sensor. The coupling arrangement of the first and second fibers to the first and second sensors may be interchanged to obtain comparative measurements for the minimization of equipment inaccuracies.

Further forms, embodiments, objects, features, aspects, advantages and benefits of the present invention shall become apparent from the detailed description and drawings of the present application.

DESCRIPTION OF PREFERRED EMBODIMENTS

Figure 1:
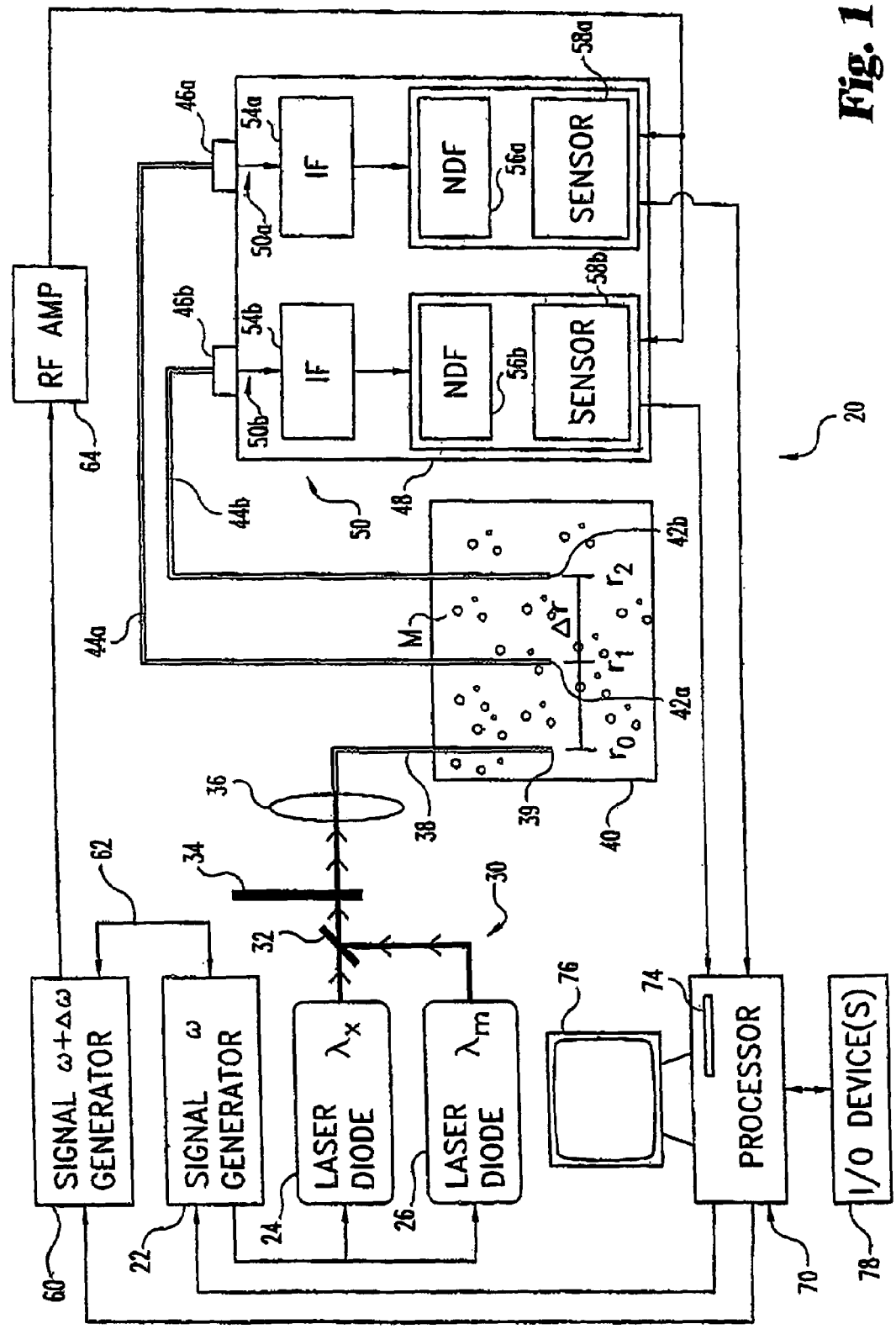
FIG. 1 is a schematic view of a system according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As used herein, "lifetime" refers to the mean survival time of an activated luminophore or the mean time between the absorption of an excitation photon and emission of a photon. Further, as used herein "multiply scattered light" refers to light that travels at least five (5) times the mean isotropic scattering length $[(1-g)\mu_s]^{-1}$; where g is the mean cosine of angular scatter and $\mu_s$ is the scattering coefficient of the medium.

FIG. 1 illustrates evaluation system 20 of one embodiment of the present invention. System 20 includes light source instrumentation 30, container 40, detection instrumentation 50, and processor 70. Light source instrumentation 30 includes modulation signal generator 22 having a range of selectable output Radio Frequencies (RF). Generator 22 dives two monochromatic light sources in the form of laser diodes 24, 26. Laser diodes 24, 26 ae intensity modulated at a selected RF frequency ($\omega$) input from generator 22 to provide light at an excitation wavelength ($\lambda_x$) and emission wavelength ($\lambda_m$), respectively. Instrumentation 30 also includes kinematic mirror 32 that is operable to successively select between the two laser beams at wavelengths $\lambda_x$, $\lambda_m$ output by the respective laser diodes 24, 26. Light from mirror 32 encounters continuously variable neutral density filter wheel 34 of instrumentation 30 to selectively adjust intensity. Lens assembly 36 of instrumentation 30 collects the light output by neutral density filter wheel 34 for input to optical source fiber 38.

Source fiber 38 enters container 40. Container 40 holds a light scattering medium M including a selected amount of a luminophore as a constituent Source fiber 38 discharges light at site 39 of medium M corresponding to the origin position to $r_0$ (r=0). Detection instrumentation 50 includes optical detector fibers 44a, 44b having respective light input sites 42a, 42b in medium M. Sites 42a, 42b are spaced apart from each other and correspond to radial distances $r_1$ and $r_2$ relative to $r_0$; where this spacing is represented by $\Delta r$ ($\Delta r = r_2 - r_1$).

Interchangeable connectors 46a, 46b couple fibers 44a, 44b to detector 48 of detection instrumentation 50. Detector 48 includes two optic channels 50a, 50b coupled by connectors 46a, 46b to receive light from detector fibers 44a, 44b, respectively. Each channel 50a, 50b has a corresponding interchangeable/removable interface filter (IF) 54a, 54b; adjustable neutral density filter (NDF) 56a, 56b; and light sensor 58a, 58b.

Light sensors 58a, 58b are coupled to processor 70 to provide one or more output signals corresponding to light detected from medium M. Sensors 58a, 58b are arranged in a standard heterodyne configuration and may be of any form such as Photomultiplier Tubes (PMTs), photodiodes, or image intensified Charge Coupled Devices (CCDs) to name just a few. For the heterodyne configuration, RF signal generator 60 is phase looked to generator 22 at a slightly different frequency $\omega + \Delta\omega$ as represented by coupling 62; where $\Delta\omega$ is the frequency difference. The output of generator 60 is amplified by RF amplifier 64 and mixed at sensors 58a, 58b to provide a corresponding differential output signal from which information corresponding to phase and modulation magnitude of the detected light can be determined with processor 70. Accordingly, processor 70 is also operatively coupled to generators 22, 60.

Processor 70 includes a port for insertion and removal of a portable memory device such as an electromagnetically or optically encoded disk, cartridge, or tape. In addition to being coupled to light source instrumentation 30 and detection instrumentation 50, processor 70 is also operatively coupled to visual display 76 and one or more Input/Output (I/O) devices 78, including for example a keyboard, mouse, light pen, acoustic loudspeakers, microphone, and/or printer just to name a few. Processor 70 may be comprised of one or more components configured as a single unit, or when of a multi-component form, processor 70 may have one or more components remotely located relative to the others, or otherwise have its components distributed throughout system 20. Processor 70 may be programmable, a state logic machine or other type of dedicated hardware, or a hybrid combination of programmable and dedicated hardware. One or more components of processor 70 may be of the electronic variety including digital circuitry, analog circuitry, or both. As an addition or alternative to electronic circuitry, processor 70 may include one or more optical elements.

Processor 70 includes an integrated and/or remote storage capability in the form of one or more types of memory. By way of nonlimiting example, this memory may include one or more of the solid-state, magnetic, and/or optical memory types. Such memory types may include Random Access Memory (RAM), Sequential Accessible Memory (SAM) (such as the First-In, First-Out (FIFO) variety, or the Last-In, First-In LIFO variety), Programmable Read Only Memory (PROM), Electrically Programmable Read Only Memory (EPROM), flash memory or Electrically Erasable Programmable Read Only Memory (EEPROM); an optical disc memory (such as a CD ROM); a magnetically encoded hard disc, floppy disc, tape, or cartridge; another variety of storage device as would occur to those skilled in the art, or a combination of any of these types. Furthermore, the memory may be volatile, nonvolatile, or a hybrid combination of volatile and nonvolatile varieties. Also, memory may be permanently installed, in a portable form that may be readily removed and reinstalled, or a combination of these types.

In one embodiment including electronic circuitry, processor 70 is of a standard personal computer configuration with a common solid-state digital integrated processing unit operatively coupled to solid-state memory. For this personal computer embodiment, appropriate interfaces are installed to facilitate control of generators 22, 60 and receipt of data from detector 48. The memory of this embodiment contains programming to be executed by the processing unit, and is arranged for reading and writing of data in accordance with one or more routines executed by processor 70. Besides memory, processor 70 may include any oscillators, control clocks, interfaces, signal compensators/conditioners, filters, limiters, Analog-to-Digital (A/D) converters, Digital-to-Analog (D/A) converters, communication ports, or other types of circuits as would occur to those skilled in the art to implement the present invention.

Figure 2A:
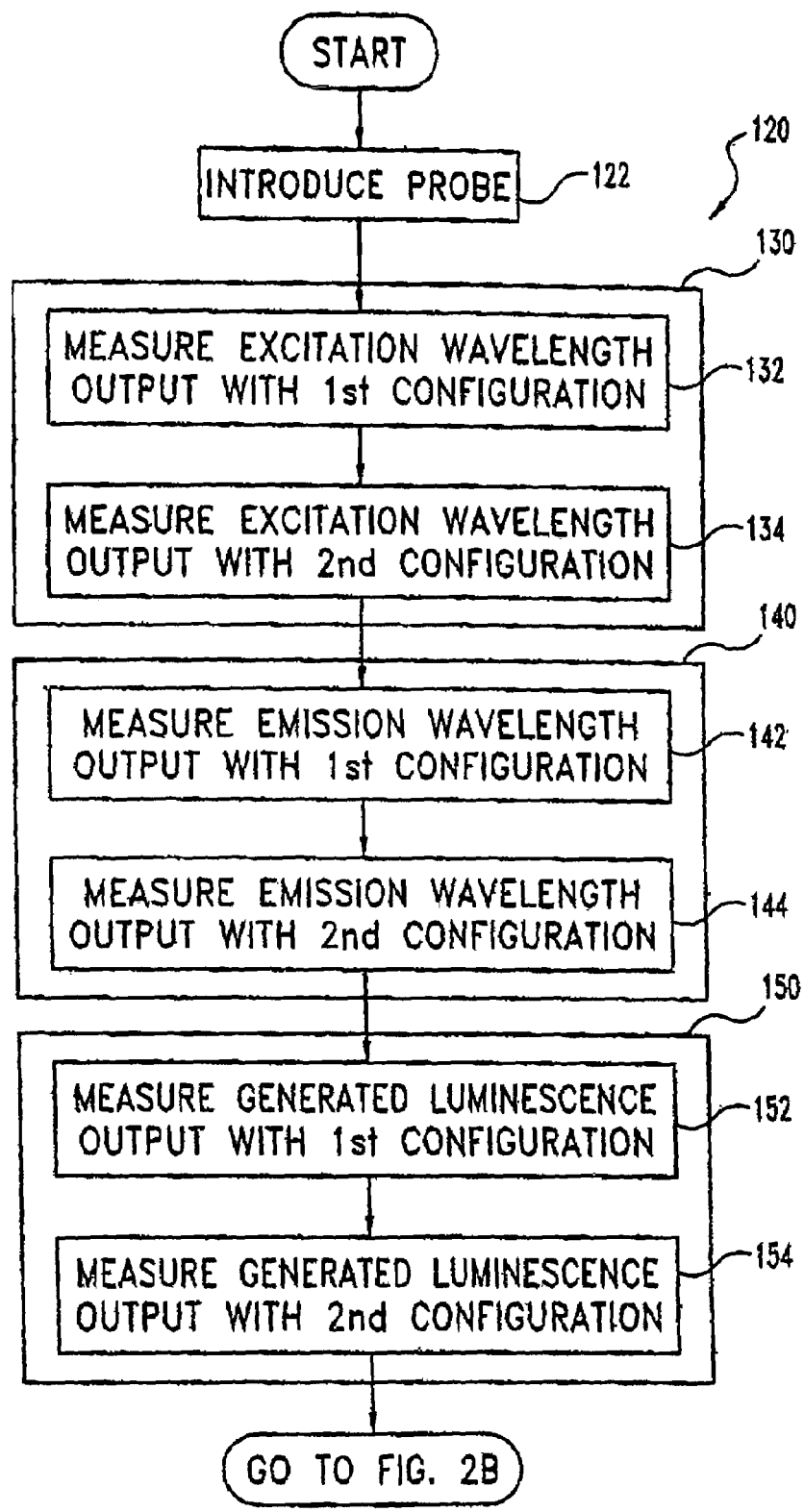
FIGS. 2A and 2B depict a flow chart illustrating one process that may be performed with the system shown in FIG. 1.
Figure 2B:
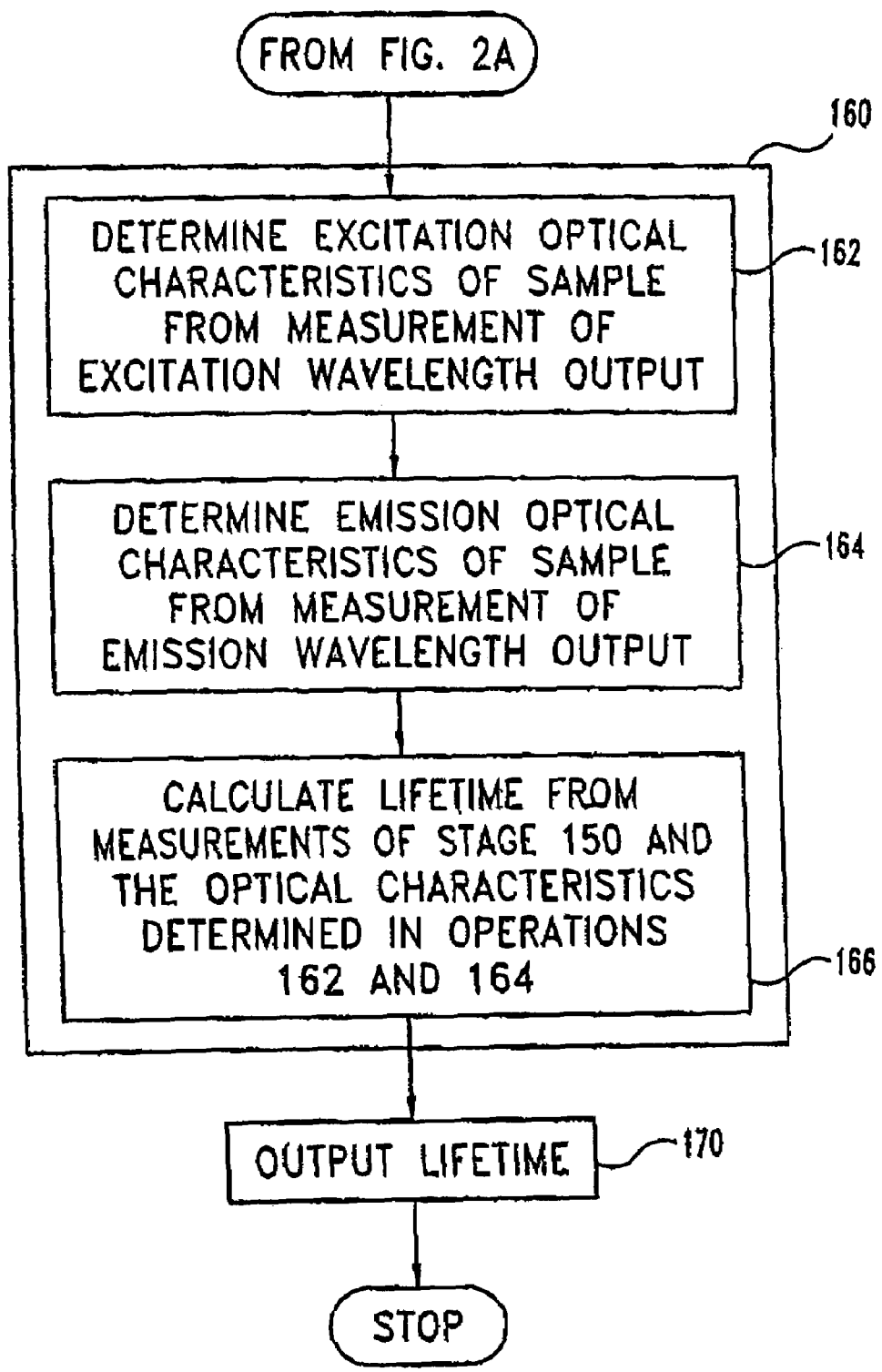

Processor 70 is configured to execute one or more routines to perform selected calculations with data received from detector 48 for lifetime evaluation process 120. Referring additionally to the flow chart of FIGS. 2A and 2B, evaluation process 120 is illustrated. Evaluation process 120 utilizes Frequency Domain Photon Migration (FDPM) techniques to extract the characteristic optical properties of medium M. These properties are obtained for photons of two wavelengths: the wavelength used to optically excite a selected luminophore and the wavelength of the luminescence resulting from this excitation. Lifetime measurements are determined from these wavelength-dependent characterizations of the medium and comparative luminescence measurements, as described hereinafter.

In stage 122 of process 120, a luminiphore probe with known excitation wavelength $\lambda_x$ and emission wavelength $\lambda_m$ is selected for evaluation and placed in light scattering medium M. This light scattering medium M may include, for example, living biologic tissue for which metabolites/analytes are being interrogated in terms of lifetime of the selected luminophore probe. In other examples, the light scattering medium M may be a cell culture, flow cytometry stream, a chemical reaction medium or other light scattering environment as would occur to those skilled in the art. In one alternative, endogenous luminophores in medium M are interrogated without introduction of an exogenous probe in stage 122.

In stage 130, intensity modulated light at frequency $\omega$ with the excitation wavelength $\lambda_x$ of the designated luminophore is provided by light source instrumentation 30 to source site 39 of medium M. Accordingly, light from laser diode 24 is provided from light source instrumentation 30 through fiber 38 to site 39. The illuminating light is subsequently scattered and/or absorbed by medium M. As multiply scattered light sourced from site 39 reaches sites 42a, 42b; it can be sensed with detection instrumentation 50 and quantitized in terms of frequency domain parameters of relative phase shift and/or modulation magnitude. Filters of detector 48 are removed and/or adjusted to facilitate detection of the excitation light wavelength with sensors 58a, 58b for this stage.

Photon transport in a light scattering medium M may be modeled as a diffusive process. In the frequency domain, the photon density $U(r,\omega)$ in a homogeneous medium at a vector position r can be related to optical properties of the medium by the diffusion equation (1) as follows:

$$-cD\nabla^2 U(r,\omega)+(c\mu_a+i\omega)U(r,\omega)-q(r,\omega); \qquad (1)$$

where: $D=[3(\mu'_s+\mu_a)]^{-1}$ is the diffusion coefficient of the medium, c is the speed of light in the medium, $q(r,\omega)$ describes properties of the light source, and $\omega$ is the modulation angular frequency of the light source (generator 22). The output signal from detection instrumentation 50, $V(r,\omega)$, depends on the complex responsivity $R(\lambda,\omega)$ expressed as: $V(r,\omega)=R(\lambda,\omega)U(r,\omega)$. The magnitude of $R(\lambda,\omega)$ represents gain and conversion efficiency of the photon transport and the angle represents the phase delay of the modulated light.

For the diffusion equation model, the absorption coefficient $\lambda_s$ and the isoptropic scattering coefficient $\mu'_s$ characterize pertinent light scattering properties of the medium at a given ght wavelength. The isotropic scattering coefficient is related to the scattering coefficient $\mu_s$ by: $\mu'_s=(1-g)\mu_s$; where g is the mean cosine of angular scatter. As used herein, the subscripts "x" and "m" are used to designate various optical parameters specific to the excitation and emission wavelengths, respectively. It has been found that lifetime measurements in a multiply scattering medium may be performed by accounting for the optical characteristics of the medium at two light wavelengths commonly associated with the luminophore: (a) the excitation wavelength $\lambda_x$ and (b) the emission wavelength $\lambda_m$. This characterization can be in terms of the absorption and isotropic scattering coefficients for each of the two wavelengths: (a) $\mu_{ax}$, $\mu'_{sx}$ for $\lambda_x$ and (b) $\mu_{am}$, $\mu'_{sm}$ for $\lambda_m$.

Accordingly, in stage 130 medium M is characterized at $\lambda_x$ beginning with operation 132. In operation 132, medium M is exposed to modulated light of wavelength $\lambda_x$ at site 39 as sourced from laser diode 24 of light source instrumentation 30. This source light can be modeled as an isotropic point source of the form: $q_x(r,\omega)=P_x(\omega)\delta(r)$; where $P_x(\omega)$ is a complex number that represents the source magnitude and phase and $\delta(r)$ is the Dirac delta function. Furthermore, by modeling the light behavior in terms of the diffusion equation with infinite boundary conditions, the solution to the diffusion equation takes the form of spherical photon density waves described by the following expression (2):

$$U_x(r,\omega) = \frac{P_x(\omega)}{4\pi c D_x r} e^{-k_x(\omega)r} \qquad (2)$$

where: $U_x(r,\omega)$ is the frequency domain excitation photon density in the medium M and the complex wave vector $k_x(\omega)$ is given by expression (3) as follows:

$$k_x^2(\omega) = \frac{\mu_{ax}}{D_x}\left(1 - i\frac{\omega}{c\mu_{ax}}\right). \quad (3)$$

On substitution of expression (3) into expression (2), the excitation photon density can be modeled as follows in expression (4):

$$U_x(r, \omega) = \frac{P_x(\omega)}{4\pi c D_x r} e^{-\beta_x(\omega)r}(\cos(\gamma_x(\omega)r) + i\sin(\gamma_x(\omega)r)) \quad (4)$$

where:

$$\alpha_x(\omega) = \left(\sqrt{\left(\frac{\mu_{ax}}{D_x}\right)^2 + \left(\frac{\omega}{cD_x}\right)^2}\right)^{1/2}$$

$$\beta_x(\omega) = \alpha_x(\omega)\cos\left(\frac{1}{2}\tan^{-1}\left(\frac{\omega}{c\mu_{ax}}\right)\right)$$

$$\gamma_x(\omega) = \alpha_x(\omega)\sin\left(\frac{1}{2}\tan^{-1}\left(\frac{\omega}{c\mu_{ax}}\right)\right).$$

The photon density is related to the observed modulation phase $\theta(r,\omega)$ by expression (5a) as follows:

$$\tan\theta(r, \omega) = \frac{\mathrm{Im}U(r, \omega)}{\mathrm{Re}U(r, \omega)}. \quad (5a)$$

The modulation $M(r,\omega)$ of the photon density waves a distance r away from and normalized to unity at the source (r=0) is related to photon density expression (5b) as follows:

$$M(r, \omega) = \sqrt{\frac{\mathrm{Re}^2 U(r, \omega) + \mathrm{Im}^2 U(r, \omega)}{\mathrm{Re}^2 U(r, 0) + \mathrm{Im}^2 U(r, 0)}}. \quad (5b)$$

For injection of source light at the excitation wavelength into the medium M in operation 132, the substitution of expression (4) into equations (5a) and (5b) results in expressions (6a) and (6b), respectively, as follows:

$$\theta_x(r,\omega) = \gamma_x(\omega)r \quad (6a)$$

$$M_x(r, \omega) = \frac{P_x(\omega)}{P_x(0)} e^{r[\alpha_x(0) - \beta_x(\omega)]}. \quad (6b)$$

The relative modulation phase and magnitude are observed with detection instrumentation 30 at the two radial distances $r_1$ and $r_2$; where $\Delta r = r_2 - r_1$, $r_2 > r_1$. The resultant phase difference is expressed as: $\Delta\theta_x(\Delta r,\omega) = \gamma_x(\omega)\Delta r$; and the resultant modulation magnitude may be as follows in expression (7):

$$M_x(\Delta r, \omega) = \frac{M_x(r_2, \omega)}{M_x(r_1, \omega)} = e^{\Delta r[\alpha_x(0) - \beta_x(\omega)]}. \quad (7)$$

where the actual modulation information observed with detection instrumentation 50 is as follows:

$$m_x(r,\omega) = M_x(r,\omega) m_{ax} m_{dx}(r,\omega) \quad (8)$$

and is related to $M_x(r,\omega)$ by the modulation of source $m_{sx}$ and the modulation response $m_{dx}(r,\omega)$ of detection instrumentation 50. The ratio of the observed modulation signals is provided by expression (9) as follows:

$$m_x(\Delta r, \omega) = \frac{m_x(r_2, \omega)}{m_x(r_1, \omega)} = \frac{m_{dx}(r_2, \omega)}{m_{dx}(r_1, \omega)} e^{\Delta r[\alpha_x(0) - \beta_x(\omega)]} \quad (9)$$

This ratio is generally independent of source modulation.

In operation 132, data is collected and stored in processor 70 corresponding to detected multiply scattered light output from medium M. It should be appreciated that only one of relative phase and modulation attenuation information needs to be observed to provide the desired characterization of the medium M at the excitation wavelength. In order to calculate both the absorption and isotropic scattering coefficients $\mu_{ax}$, $\mu'_{sx}$ with expression (4) from relative phase or magnitude observations, a regression or other iterative estimation can be employed. To facilitate this calculation, operation 132 detects multiply scattered light outputs for a number of different RF modulation frequencies.

While relative measures of phase or modulation attenuation are indicative of photon-migration through medium M, differences in the response function of channels 50a and 50b of detector 48 may result in inaccuracy that reaches an undesirable level for some applications. It has been found that instrumentation response function effects may be reduced by switching from the illustrated (first) configuration with sites 42a, 42b respectively coupled to channels 50a, 50b to a second configuration with sites 42a, 42b coupled to channels 50b, 50a; and repeating the phase and/or modulation magnitude measurements of operation 132 in operation 134 with the second configuration. The measurements of operation 134 are conducted with the same relative spacing between sites 39, 42a, and 42b. Connectors 46a, 46b provide a convenient way to manually perform this reconfiguration. In an alternative embodiment, an optical multiplexer may be utilized to automatically accomplish this reconfiguration under the control of processor 70.

In an example based on relative phase measurements, the effective response function of the detection instrumentation is designated $\theta_{instr}$. Letting $\Delta\theta_x(r_2 r_1) = \theta_x(r_2) - \theta_x(r_1) + \theta_{instr}$ represent measurements during operation 132 and $\Delta\theta_x(r_1 r_2) = \theta_x(r_1) - \theta_x(r_2) + \theta_{instr}$ represent measurements during operation 134, the instrument effects can be removed by taking one half of the difference between these two relative measurements. The desired phase difference, $\Delta\theta_x$, is then expressed as: $\Delta\theta_x = 0.5[\Delta\theta_x(r_2 r_1) - \Delta\theta_x(r_1 r_2)]$.

Measurements gathered with detection instrumentation 50 in operations 132, 134 of stage 130 for a desired number of different modulation frequencies are recorded with processor 70. Stage 140 is next encountered to obtain an optical characterization of medium M at the emission wavelength $\lambda_m$ in terms of absorption and isotropic scattering coefficients $\mu_{am}$, $\mu'_{sm}$. In operation 142, emission wavelength light is provided to source site 39 with laser diode 26 of light source instrumentation 30, instead of excitation wavelength light from laser diode 24. Filtering of detector 48 is removed/adjusted to facilitate detection of multiply scattered light output from medium M at the emission wavelength $\lambda_m$ and measurement of relative modulation phase or magnitude over a selected range of modulation frequencies in the manner described for stage 130. The emission photon density is characterized in stage 140 in accordance with expressions (2)–(9) substituting the emission wavelength for the excitation wavelength (and correspondingly substituting subscript "x" with "m" in these expressions). In operation 144, the measurements are repeated with coupling of site 42a being switched to sensor 58b of channel 50b and coupling of site 42b being switched to sensor 58a of channel 50a. The measurements of operations 142, 144 are recorded with processor 70 to determine absorption and isotropic scattering coefficients $\mu_{am}$, $\mu'_{sm}$.

In stage 150, luminescence data is gathered. Excitation wavelength light is provided to site 39 of medium M from laser diode 24 of light source instrumentation 30 in operation 152 of stage 150 and frequency domain measurements are gathered. For stage 150, detection instrumentation 50 is configured with filtering of channel 50a adjusted/removed to detect the excitation wavelength with sensor 58a and filtering of channel 50b adjusted/removed to detect the excitation wavelength with sensor 58b. For a fluorescent type of luminophore, fluorescence photon density may be modeled in accordance with expression (10) as follows (where the subscript "f" denotes fluorescence optical parameters):

$$U_l(r, \omega) = \frac{\phi \mu_{af} P(\omega)}{4\pi c D_x D_m r} \left( \frac{e^{-k_x(\omega)r} - e^{-k_m(\omega)r}}{k_m^2(\omega) - k_x^2(\omega)} \right) \left( \frac{1 + i\omega\tau}{1 + (\omega\tau)^2} \right). \quad (10)$$

The quantum efficiency of the fluorophore is denoted by $\phi$ and $\mu_{ef}$ describes absorption of excitation light due to fluorescence. Fluorescence decay is assumed to be of the monoexponential type with lifetime $\tau$; however, the principles of the present invention can be applied to multiexponential decays using techniques known to these skilled in the art. Using expression (3), the fluorescence photon density of expression (10) can be written as presented in the following expression (11):

$$U_l(r, \omega) = \frac{\phi \mu_{af} P(\omega)}{4\pi c D_z D_m [1 + (\omega\tau)^2] r} \{[\psi(r, \omega) - \kappa(r, \omega)\omega\tau] + l[\kappa(r, \omega) + \psi(r, \omega)\omega\tau]\}, \quad (11)$$

where:

$$\psi(r, \omega) = \frac{\delta(r, \omega)\xi + \zeta(r, \omega)\rho(\omega)}{\xi^2 + [\rho(\omega)]^2},$$

$$\kappa(r, \omega) = \frac{\zeta(r, \omega)\xi - \delta(r, \omega)\rho(\omega)}{\xi^2 + [\rho(\omega)]^2},$$

$$\delta(r, \omega) = \exp[-\beta_z(\omega)r]\cos[\gamma_z(\omega)r] \sim \exp[-\beta_m(\omega)r]\cos[\gamma_m(\omega)r],$$

-continued $$\zeta(r, \omega) = \exp[-\beta_z(\omega)r]\sin[\gamma_z(\omega)r] = \exp[-\beta_m(\omega)r]\sin[\gamma_m(\omega)r],$$

$$\xi = \frac{\mu_{am}}{D_m} - \frac{\mu_{ax}}{D_x},$$

$$\rho(\omega) = \frac{\omega}{c}\left(\frac{1}{D_z} - \frac{1}{D_m}\right).$$

The fluorescence photon density is related to the observed fluorescence modulation phase $\theta_f(r,\omega)$ by expression (5a). Substituting expression (11) into expression (5a), expression (12) results as follows:

$$\tan\theta_f(r, \omega) = \frac{\kappa(r, \omega) + \psi(r, \omega)\omega\tau}{\psi(r, \omega) - \kappa(r, \omega)\omega\tau}, \quad (12)$$

and the fluorescence decay lifetime can be written per expression (13) as follows:

$$r = \frac{1}{\omega} \frac{\tan\theta_f(r, \omega) - \eta(r, \omega)}{\eta(r, \omega)\tan\theta_f(r, \omega) + 1}, \quad (13)$$

where $\eta(r,\omega)=\kappa(r, \omega)/\psi(r,\omega)$ and determinations of $\psi(r,\omega)$ and $\kappa(r, \omega)$ are based on measured phase shifts $\Delta\theta_x(\Delta r,\omega)$ and $\Delta\theta_f(\Delta r,\omega)$.

Alternatively, the fluorescence photon density is related to fluorescence modulation $M_f(r,\omega)$ by expression (5b). Substituting expression (11) into expression (5a) and noting that $\kappa(r, 0)=0$ yields expressions (14) and (15) as follows:

$$M_f(r, \omega) = \frac{P(\omega)}{P(0)} \sqrt{\frac{\epsilon(r_2, \omega)}{(1 + (\omega\tau)^2)}} \quad (14)$$

where:

$$\varepsilon(r_2, \omega) = \frac{\psi^2(r_2, \omega) + \kappa^2(r_2, \omega)}{\psi^2(r_2, 0)} \quad (15)$$

is based upon the optical coefficients of the sample. Comparable expressions can be derived for other types of luminescence and different boundary conditions.

After measurements of relative modulation phase or magnitude are made in operation 152, the measurements are repeated in operation 154 with sites 42a, 42b being switched relative to channels 50a, 50b as described in connection with operation 134 and 144. As part of the reconfiguration for stage 154, the filtering of channels 50a, 50b is also adjusted to facilitate detection of the excitation wavelength with sensor 58b and the emission wavelength with sensor 58a. Measurements of operations 152, 154 are stored with processor 70.

In calculation stage 160 (FIG. 2B) of evaluation process 120, processor 70 performs calculations with the data collected during stages 130, 140, 150. In operation 162, processor 70 performs regression analysis of measurements from excitation characterization stage 130 to determine the absorption and isotropic scattering coefficients $\mu_{ax}$, $\lambda'_{sx}$ at the excitation wavelength. In operation 164, processor 70 performs regression analysis of measurements from emission characterization stage 140 to determine the absorption and isotropic scattering coefficients $\mu_{am}$, $\mu'_{sm}$ at the emission wavelength.

In operation 166, processor 70 calculates lifetime based on the measurements obtained from luminescence characterization stage 150 and the coefficients obtained from operations 162, 164. For calculations of lifetime based on relative phase measurements in stage 150, the measured phase shift $\Delta\theta_f(\Delta r,\omega)=\theta_f(r_2,\omega)-\theta_x(r_1,\omega)$ is adjusted by the addition of phase change $\theta_{xc}(r_1,\omega)$ associated with the excitation propagation from site 39 to site 42a at $r_1$. This phase value $\theta_{xc}(r_1,\omega)$ can be calculated from expression (6a) and the optical characteristics determined in operation 162 from measurements of excitation wavelength characterization stage 130. The resultant modulation phase $\theta_f(r_2,\omega)=\Delta\theta_f(\Delta r,\omega)+\theta_{xc}(r_1,\omega)$ is the phase at the source (r=0) and can be used in expression (13) to determine lifetime $\tau$.

For calculation of lifetime based on modulation attenuation, the modulation magnitude at radial distance $r_2$ is referenced relative to the excitation modulation magnitude at radial distance $r_1$. The ratio of epression (14) to expression (6b) yields expression (16) and (17) as follows:

$$M_f(\Delta r_1 \omega) = \frac{M_f(r_2, \omega)}{M_x(r_1, \omega)} = \frac{1}{e^{r_1[\alpha_z(0)-\beta_z(\omega)]}} \sqrt{\frac{\epsilon(r_2, \omega)}{(1+(\omega\tau)^2)}} \quad (16)$$

from lifetime $\tau$ is derived:

$$r = \frac{1}{\omega}\sqrt{\frac{\epsilon(r_2, \omega)}{M_f^2(\Delta r, \omega)e^{2r_1[\alpha_z(0)-\beta_z(\omega)]}} - 1}. \quad (17)$$

The modulation magnitude detected with detection instrumentation 50 is given by expression (18) as follows:

$$m_f(r_2,\omega) = M_f(r_2,\omega) m_{sc}\, m_{dm}(r_2,\omega) \quad (18)$$

which is related to modulation $M_f(r_2,\omega)$ by modulation $m_{sx}$ of the source at the excitation wavelength, and the modulation $m_{dm}(r_2,\omega)$ of the detection instrumentation 50 at the emission wavelength. The ratio of expression (18) and the excitation modulation of expression (8) is provided by expression (19) as follows:

$$m_f(\Delta r, \omega) = \frac{m_f(r_2, \omega)}{m_x(r_1, \omega)} = \frac{M_f(r_2, \omega)}{M_x(r_1, \omega)} \frac{m_{dm}(r_2, \omega)}{m_{dx}(r_1, \omega)}. \quad (19)$$

From the ratio of expression (19), the following expression (20):

$$M_f(\Delta r, \omega) = m_f(\Delta r, \omega) \frac{m_{dx}(r_1, \omega)}{m_{dm}(r_2, \omega)} \quad (20)$$

is found to depend upon the ratio of the detection instrumentation 50 response functions at excitation and emission wavelengths. This information may be expressed as a single ratio of modulations of the sources; where given the optical coefficients of the medium M from operations 162 and 164, excitation $M_{xc}(r,\omega)$ and emission $M_{mc}(r,\omega)$ can be determined from expression (7). The product of source modulation and detection instrument response function can be determined from expression (8) at the excitation:

$$m_{ax} m_{dx}(r_1, \omega) = \frac{m_x(r_1)}{M_{xa}(r_1, \omega)} \quad (21)$$

and emission:

$$m_{am}, m_{dm}(r_2, \omega) = \frac{m_m(r_2)}{M_{ma}(r_2, \omega)} \quad (22)$$

wavelengths. The resulting ratio of detection instrument response functions is given by expression (23) as follows:

$$\frac{m_{dx}(r_1, \omega)}{m_{dm}(r_2, \omega)} = \frac{m_{am}}{m_{ax}} \frac{m_x(r_1, \omega)}{m_m(r_2, \omega)} \frac{M_{ma}(r_2, \omega)}{M_{xa}(r_1, \omega)} \quad (23)$$

which depends upon a comparison between measured and calculated modulation information and a constant ratio of modulations of the sources at emission and excitation wavelengths. Varying the source modulation ratio, the lifetime measured at multiple modulation frequencies can be regressed to obtain a unique source modulation ratio associated with a vanishing slope, i.e. minimized $\chi^2$ of the lifetime distribution, and to obtain the resulting lifetime $\tau$. After lifetime is determined in stage 160 from relative phase or modulation measurements, it is output in stage 170, concluding process 120.

It should be understood that only one possible sequence of the measurement stages 130, 140, 150 is illustrated. Indeed, the various measurements may be performed in many other sequences with respect to selected light wavelengths, modulation frequencies, and coupling configuration of sites 42a, 42b relative to channels 50s, 50b. Also, the calculations of stage 160 may be performed any time by processor 70 in relation to the measurement stages 130, 140, 150 to the extent measurement data has been provided to processor 70.

In other embodiments, the arrangement of system 20 may differ. For example, light source instrumentation may include a source of excitation and/or emission wavelength light such as a different type of laser, lamp, or other device as would occur to those skilled in the art. In another example, detection instrumentation 50 may include an optical multiplexer controlled by processor 70 to provide for the switching of optical coupling relative to detector 48. In one alternative embodiment, the measurements may be based on two spaced apart light source sites 39 in medium M with just one detection site 42a or 42b and corresponding sensor 58a or 58b. In one form of this arrangement, light source instrumentation may be configured with another set of the components described for instrumentation 30 to provide two light source channels; while detection instrumentation 50 could be modified to include only a single channel 50a or 50b. The lifetime calculations may be readily adapted to this dual source using techniques known to those skilled in the art. Also, instrument function that might lead to calculation discrepancies relative to the two source sites can be addressed by switching the equipment supplying light to each source; thereby providing the first and second measurement configurations described in connection with stages 130, 140, 150.

Figure 3:
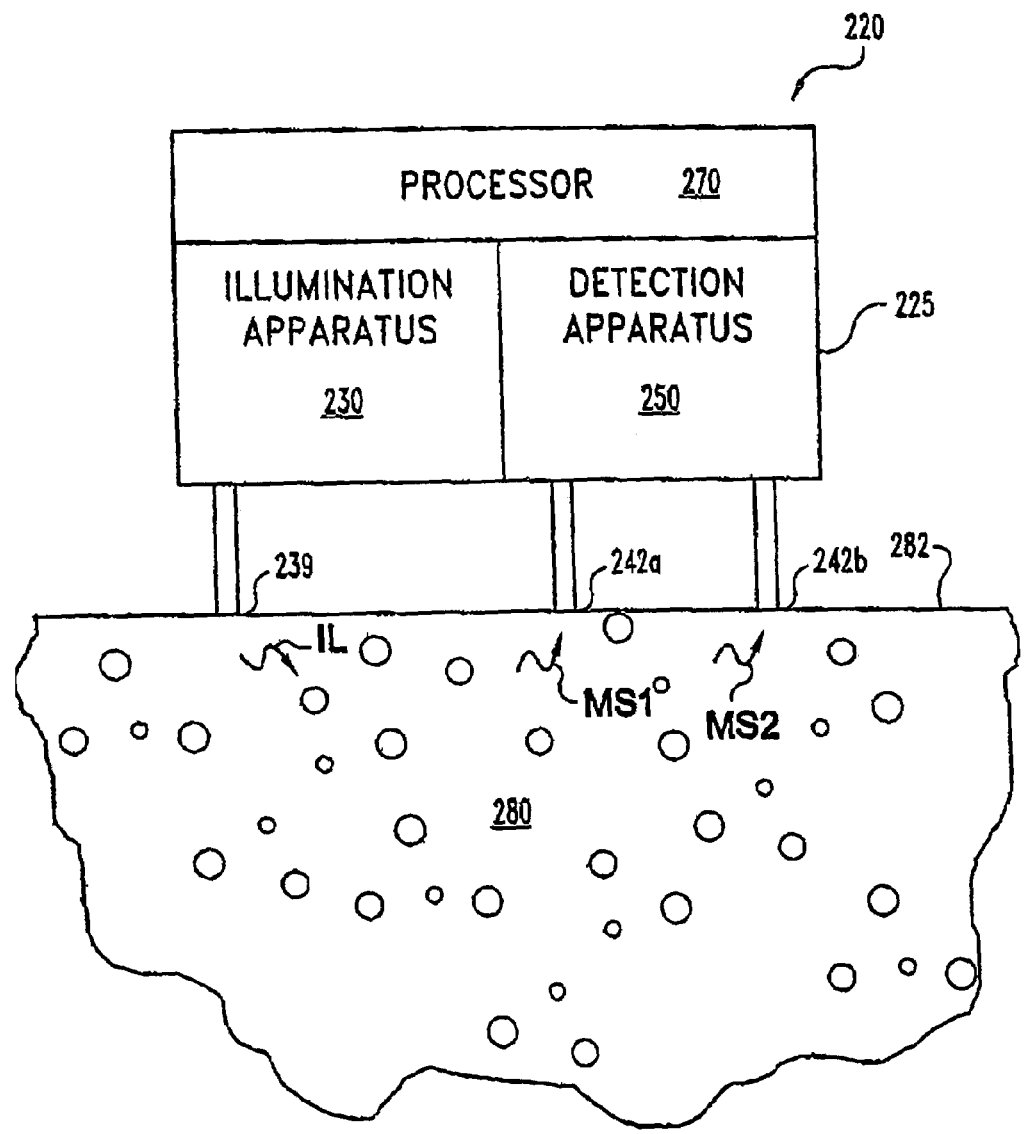
FIG. 3 is a schematic view of a system of another embodiment of the present invention.

FIG. 3 depicts medical diagnostic system 220 of another embodiment of the present invention. System 220 includes diagnostic instrument 225 to evaluate a patient's medical condition based on lifetime readings of an endogenous, exogenous, or immobilized exogenous fluorophore in a patient's tissue 280. Instrument 225 includes light source apparatus 230, detection apparatus 250, and processor 270 that are operationally configured like light source instrumentation 30, detection instrumentation 50, and processor 70, respectively, but are packaged in a manner convenient for in vivo interrogation of tissue 280.

The fluorophore in tissue 280 is typically an exogenous probe introduced into tissue 280 that has a known excitation and emission wavelength to which the optics of instrument 225 are matched. Such exogenous probes may be immobilized in a subcutaneous implant, by oral ingestion, or any other means that would occur to those skilled in the art. Alternatively or additionally, the present application may be applied to monitor endogenous fluorophores for which excitation/emission wavelengths are known.

Light source apparatus 230 includes one or more sources to provide light to tissue 280 at excitation and emission wavelengths for the selected fluorophore in accordance with evaluation process 120. The source light is provided to site 239 of tissue 280 as represented by arrow IL. The source light is multiply scattered by tissue 280 and received by detection apparatus at sites 242a, 242b as represented by arrows MS1, MS2. Instrument 225 is configured to maintain a generally constant relative spacing between sites 239, 242a, 242b, corresponding to $r_0$, $r_1$, and $r_2$, respectively. Processor 270 may be configured to control selection of the appropriate source light wavelength and modulation frequencies for light source apparatus 230 and the corresponding filter configuration for detection apparatus 250 to automatically perform the stages and operations of process 120 with instrument 225.

For external interrogations, instrument 225 may include a moveable hand-held wand or optical probe coupled to a base unit; where the wand is arranged for placement proximate to surface 282 of tissue 280. In this case, surface 282 may be the patients skin, with instrument 225 being arranged to make percutaneous measurements. In other instances, instrument 225 may include an endoscope coupled to a base unit that is to perform interrogations through a body lumen, cavity, or small surgical incision. For these instances, surface 282 can be the boundary of the body lumen or an organ selected for interrogation, to name just a few examples. Depending on the configuration of instrument 225, the calculations performed in stage 160 may be adjusted to account for finite boundary conditions to improve performance. In another embodiment, instrument 225 is arranged to place sites 239, 242a, 242b in the tissue, more closely approximating infinite boundary conditions. Furthermore, in alternative embodiments, instrument 225 may be completely contained in a portable device that is battery powered.

Yet another embodiment includes interrogating a light scattering medium including an amount of a selected luminophore with light at an emission wavelength of the luminophore and sensing multiply scattered light at the emission light wavelength in response to this interrogation to provide a first optical characterization of the medium. The medium is also exposed to light at an excitation wavelength of the luminophore and a multiply scattered luminescence at the emission wavelength is detected in response to this exposure. A value corresponding to lifetime of the luminophore is determined from the first optical characterization and the luminescence.

A further embodiment includes exposing a light scattering medium including an amount of a luminophore to a number of different light wavelengths selected relative to the luminophore. A plurality of optical characteristics of the medium are established by sensing multiply scattered light at each of the different wavelengths. A value corresponding to lifetime of the luminophore is determined from the optical characteristics and a multiply scattered emission at a first one of the light wavelengths caused by exposure of the medium to a second one of the light wavelengths.

Still a further embodiment provides for an evaluation of a light scattering medium including an amount of a luminophore with a light interrogation system. This system includes a first device optically coupled to a first site of the medium and a second device optically coupled to a second site of the medium that is spaced apart from the first site. Also included are subjecting the medium to a first light wavelength selected relative to the luminophore, optically coupling the first device to the second site and the second device to the first site, and exposing the medium to the first light wavelength after coupling. A value corresponding to lifetime of the luminophore is determined from a first light output and a second light output.

Another embodiment includes means for illuminating a light scattering medium including a luminophore; means for characterizing light scattering behavior of the medium for an excitation wavelength of the luminophore and an emission wavelength of the luminophore; and means for determining lifetime of the luminophore from the characterizing means and a multiply scattered light emission from the medium at the emission wavelength in response to illumination by light at the excitation wavelength.

Also, because luminophores may have different activated states, they may have multiple lifetimes corresponding to these states. While the examples described herein are directed to the lifetime of luminophores that are excited to a single activated state to preserve clarity, in other embodiments the principles of the present invention can be applied to luminophores with multiple activated states and lifetimes using techniques known to those skilled in the art. Such multiple lifetime probes are also within the scope of the present invention.

EXPERIMENTAL EXAMPLES

The present invention will be further described with reference to the following specific examples. These experiments and results are intended to be illustrative of the present invention and should not be considered limiting or restrictive with regard to the scope of the present invention. Further, any theory, mechanism of operation, proof, or finding stated herein is meant to further enhance understanding of the present invention and is not intended to make the present invention in any way dependent upon such theory, mechanism of operation, proof, or finding.

Several experiments were conducted with a test setup comparable to system 20. FDPM measurements according to process 120 were conducted in a light scattering tissue-simulating phantom from of medium M. For these experiments the lifetimes of different micromolar concentrations of two luminophors of the fluorescent type where evaluated: (1) 3,3'-Diethylthiatricarbocyanine Iodide (DTTCI) and (2) Indocyanine Green (ICG or IR-125) (both from AR-COS Organics, Fair Lawn, N.J.). Container 40 for the phantom was a cylindrical acrylic vessel 11.3 cm in diameter and 15 cm in height. The phantom was prepared as an aqueous (DUIF water; Fisher Scientific, Fair Lawn, N.J.) intralipid (20%; Pharmacia & Upjohn Company, Clayton, N.C.) solution to mimic tissue-like scattering properties. A DTTCI stock solution was prepared with ethanol; and ICG was dissolved directly in water. Appropriate quantities of stock solutions were suspended in 1.0% Intralipid to yield the final fluorophore concentrations in the phantoms as listed in Table 1 that follows:

detector fibers 44a, 44b were terminated with connectors 46a, 46b in the form of SMA fiber-optic connectors that could be interchanged conveniently to perform the reconfigurations of stages 130, 140, 150.

Detector 48 included neutral-density filters 56a, 56b from CVI Laser Corporation, Albuquerque, N.M. and interference filters 54a, 54b of a narrow-bandpass form (10 nm FWHM; CVI Laser Corporation). Also included were lens assemblies that focused the collected light onto the PMTs. The gain settings of the PMTs remained unchanged during all measurements. The three neutral-density filters in the setup aided in maintaining constant dc levels of the detected PMT signals. The filters 34, 54a, 54b were used to adapt the setup to different output power levels of the two source laser diodes 24, 26 and to facilitate acquisition of light intensity signals over a large dynamic range. The PMTs were gain modulated at the modulation frequency of the laser diodes plus an offset frequency of 100 Hz ($\Delta\omega$). The heterodyned PMT signals were then digitized, Fourier transformed, and analyzed for phase shift and amplitude attenuation by use of

| Dye | Conc. [μM] | $\lambda_x$ [nm] | $\mu_{ax}$ [1/cm] | $\mu_{ax}'$ [1/cm] | $\lambda_m$ [nm] | $\mu_{am}$ [1/cm] | $\mu_{am}'$ [1/cm] | $\tau$ [ns] |
|---|---|---|---|---|---|---|---|---|
| DTTCI | 0.5 | 749 | 0.054(8) | 9.2(12) | 828 | 0.032(3) | 10.2(8) | 1.34(3) |
|  | 1.0 | 749 | 0.07(2) | 6.8(15) | 828 | 0.031(3) | 8.4(7) | 1.34(4) |
| ICG | 0.0625 | 778 | 0.039(8) | 9.5(13) | 828 | 0.033(4) | 8.0(8) | 0.54(3) |
|  | 0.125 | 778 | 0.05(1) | 7.9(20) | 828 | 0.051(9) | 9.2(15) | 0.56(4) |

Figure 4:
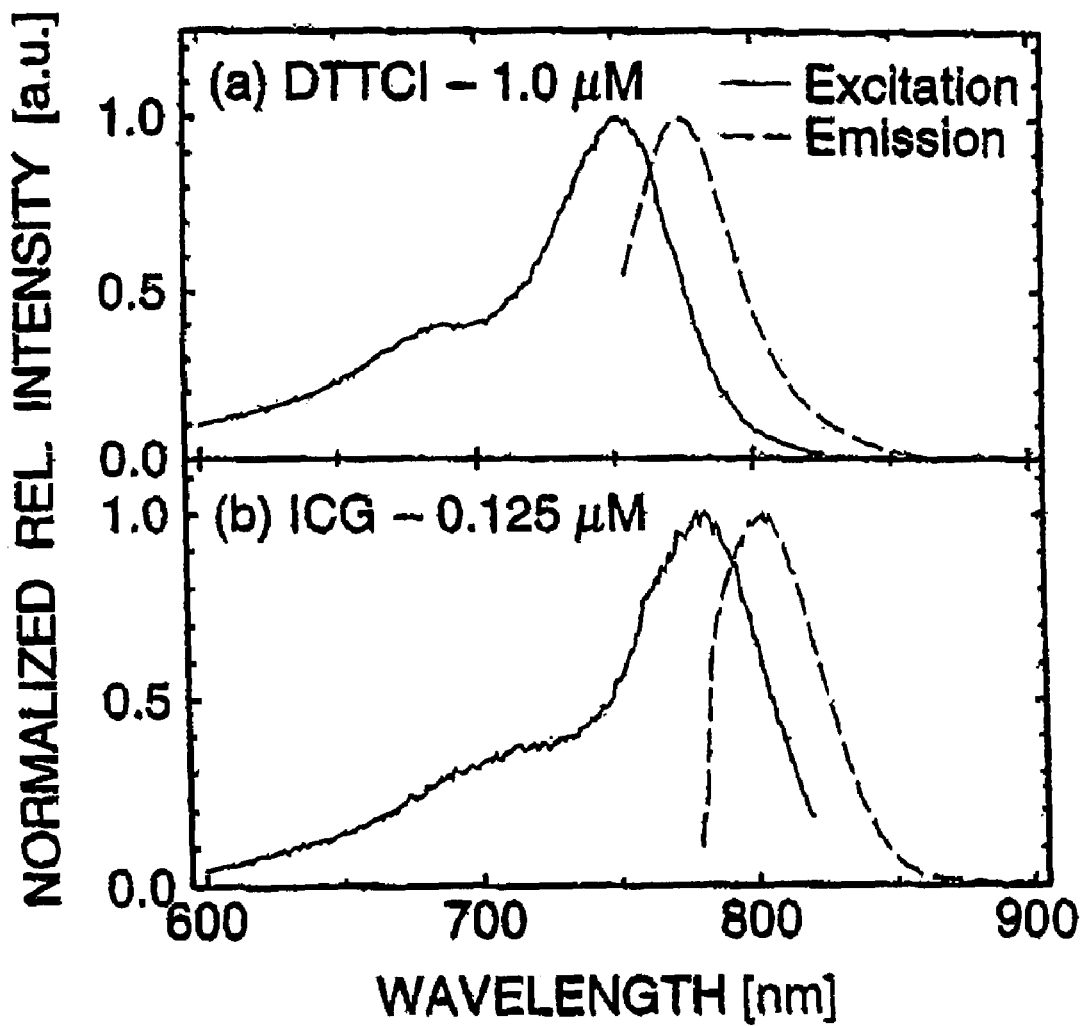
FIG. 4 depicts normalized excitation and emission spectra for DTTCI (top) and ICG (bottom) in a comparative format pertinent to experimental examples.

Additional samples were prepared in water for spectral analysis. FIG. 4 shows the concentrations of the analyzed dyes and presets the relevant excitation and an emission spectra measured with a spectrofluorometer (Fluorolog-2; SPEX Industries, Inc., Edison, N.J.)

The lifetime of DTTCI dissolved in ethanol was previously reported as 1.33±0.02 ns at 790-nm excitation and 820-nm emission wavelengths. The lifetime of ICG was reported to be 0.57±0.02 ns at 780-nm excitation and 830-nm emission wavelengths measured without scattering by use of time-domain techniques as well as by conventional frequency-domain fluorimetry referenced against the known lifetime of a well-characterized fluorophore.

For the experimental examples, excitation wavelengths were provided by laser diodes of the 56 DFS series; Melles Griot, Boulder, Colorado with power/wavelengths of 3 mW at 749 nm for ICG excitation and 25 mW at 718 nm for DTTCI excitation. A 30 mW 830 nm laser diode from Melles Griot was used for emission wavelengths. Kinematic mirror 32 was a model 9891 from New Focus, Santa Clara and neutral density filter wheel 34 as from Newport of Irvine, Calif. Source fiber 38 was 1000-μm-core source fiber (3M FT SILICA/0.39-NA TECS multimode fiber type). Also, fibers 44a, 44b were provided by two additional 1000-μm-core fibers of identical length placed in medium M at equal depth and parallel to source fiber 38. Detector fibers 44a, 44b were positioned within the sample at distances $r_1$=1.0 cm and $r_2$=2.5 cm away from source fiber 38. The radial separation distance ($\Delta r$=1.5 cm) of the two detection fibers remained unchanged during all measurements. The light sensed by the fibers was delivered to sensors 58a, 58b in the form of grain-modulated photomultiplier tube (PMT) detectors Model H6573; Hammamatsu, Bridgewater, N.J.). The Lab VIEW software (National Instruments Corporation, Austin, Tex.) executed by a personal computer form of processor 70.

Figure 5:
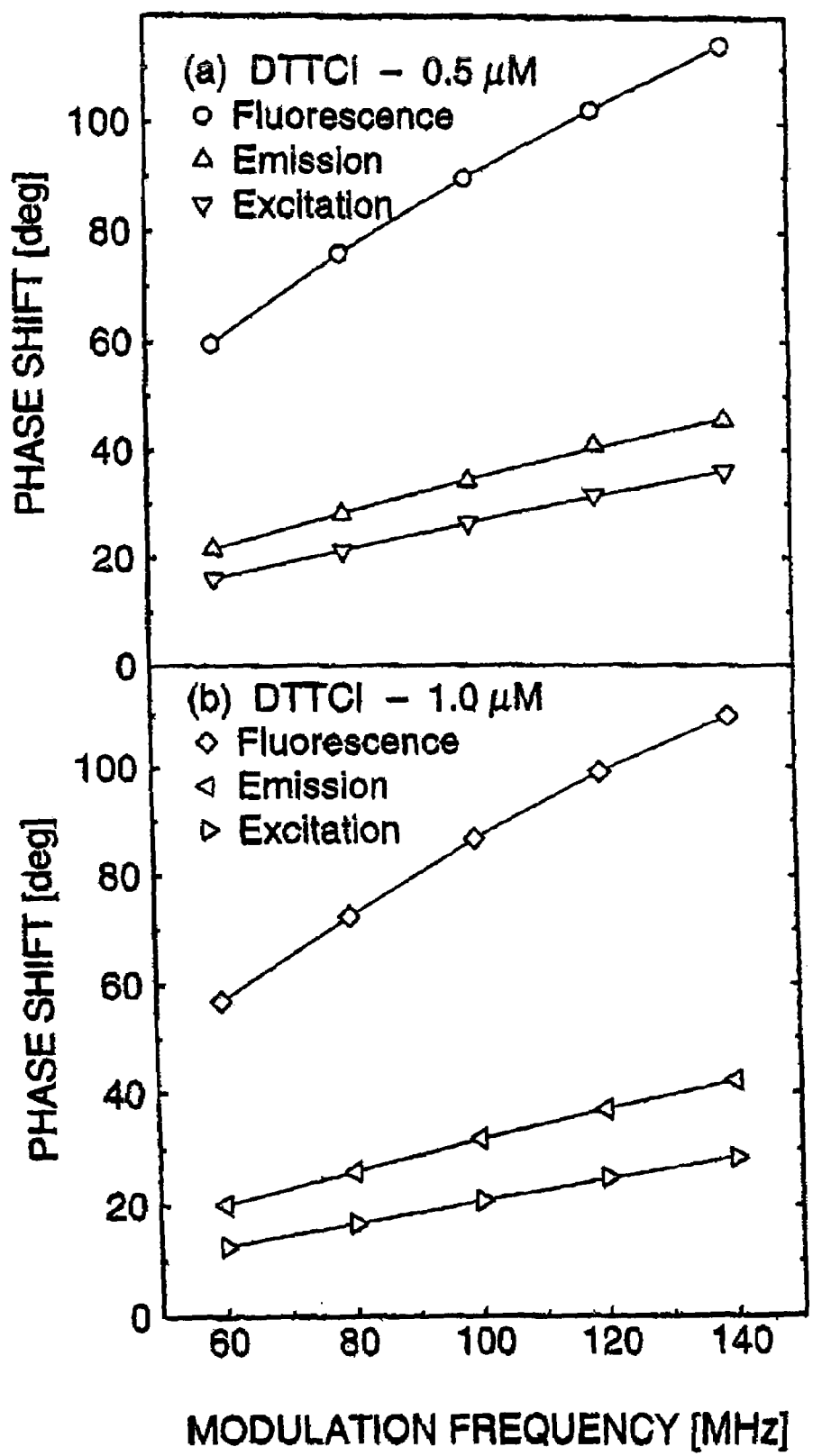
FIG. 5 plots phase shift versus modulation frequency for two different concentrations of DTTCI in a comparative format pertinent to experimental examples.
Figure 6:
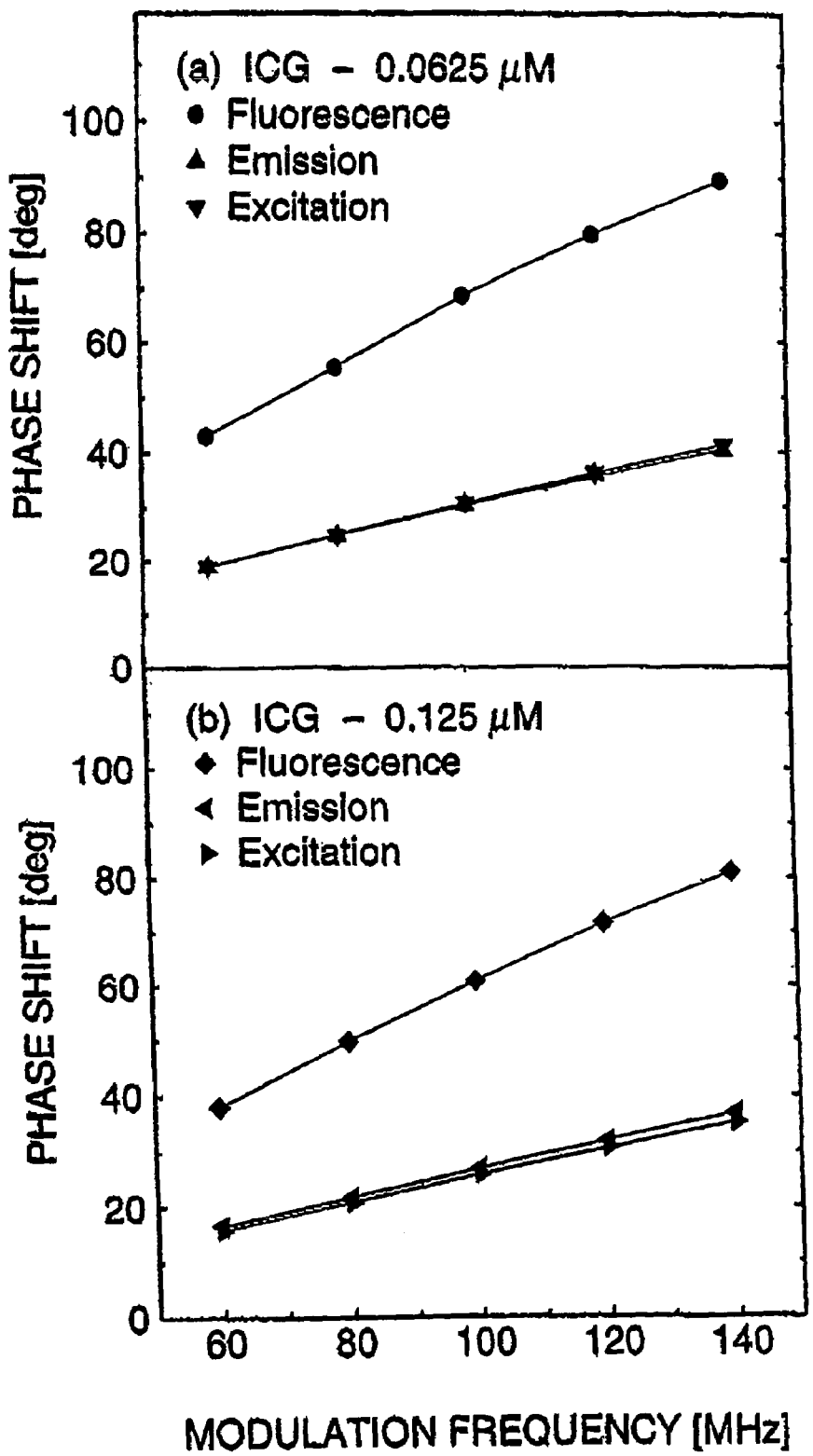
FIG. 6 plots phase shift versus modulation frequency for two different concentrations of ICG in a comparative format pertinent to experimental examples.
Figure 7:
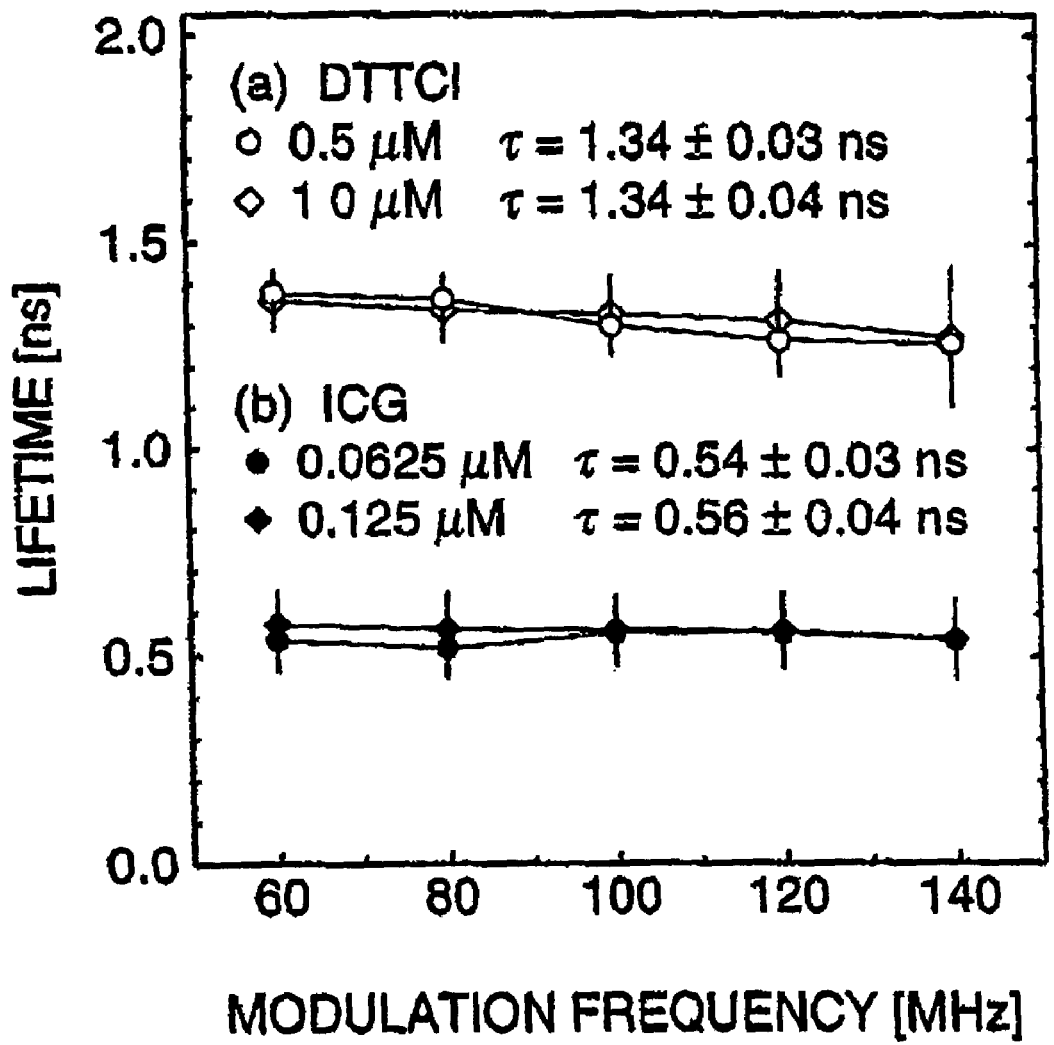
FIG. 7 plots lifetime versus modulation frequency for DTTCI and ICG corresponding to the plots of FIGS. 5 and 6.

The experimental results illustrated in FIGS. 5–7 are based on relative phase measurements in stages 130, 140, 150. To obtain these results the stages were performed in a different order than illustrated in the flow chart of FIGS. 2A and 2B. Namely, Stage 150 was performed first, followed by stage 130, and then stage 140. The measurement protocol for the lifetime determination comprises the three stages 130, 140, 150 for each concentration; where each stage includes measurements for two different configurations over a range of modulation frequencies from about 60 to about 140 MegaHertz (MHz). The kinematic mirror placed in the experimental setup expedited execution of the three stages of each measurement. Optical parameters of the sample at excitation and emission wavelengths were obtained from two-parameter least-squares fits of expression (5) to the excitation and the emission data, respectively. These optical coefficients together with the fluorescence phase shift then permitted the deduction of the lifetime of the fluorescent dye from expression (13).

The top graph (a) of FIG. 5 provides experimentally determined plots of phase shift versus modulation frequency for a 0.5 μM concentration of DTTCI with the excitation characterization measurements of stage 130, the emission characterization measurements of stage 140, and the fluorescence characterization measurements of stage 150 shown in ascending order. The bottom graph (b) of FIG. 5 provides plots of the same type and in the same order as top graph (a) for a 1.0 μM concentration of DTTCI. The top graph (a) and the bottom graph (b) of FIG. 6 provide excitation, emission, and fluorescence characterization plots in the same order as the graphs of FIG. 5 for 0.0625 μM and 0.125 μM concentrations of ICG, respectively, FIG. 7 plots the lifetime calculation results of stage 160 for the two concentrations for DTTCI (hollow symbols) and ICG (solid symbols) as based on the measurements illustrated in FIGS. 5 and 6. It should be understood that optical parameters of the samples were not known a priori, and lifetime determinations were made without a reference luminophore, being based instead on the phase-shift measurements shown. Results of the two-parameter fits of expression (5) to the phase-shift data are indicated by curves that join the data symbols obtained at the excitation and the emission wavelengths. The optical coefficients extracted for the samples containing the various concentrations of DTTCI or ICG are summarized in Table 1.

Figure 8:
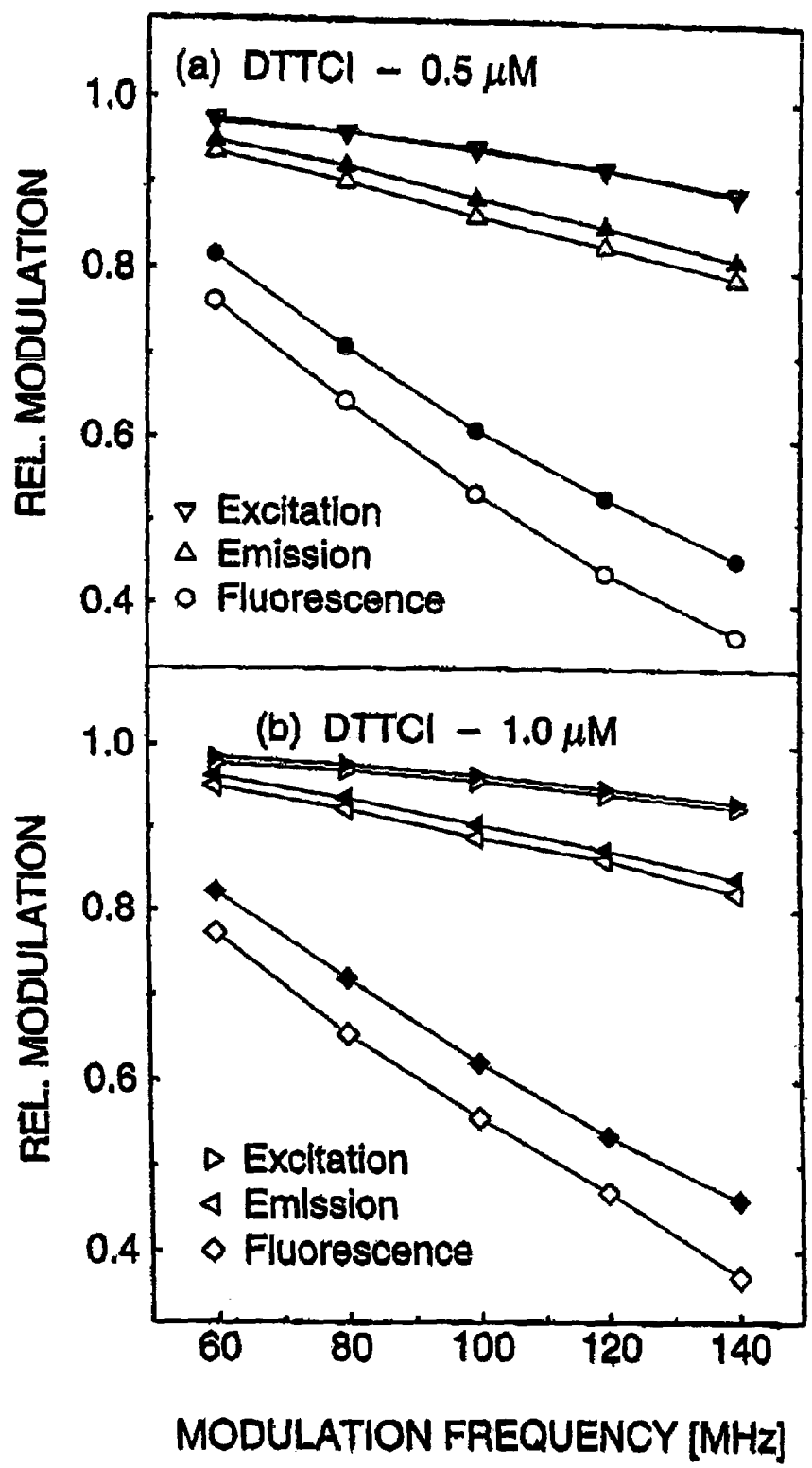
FIG. 8 plots relative modulation attenuation versus modulation frequency for two different concentrations of DTTCI in a comparative format pertinent to experimental examples.
Figure 9:
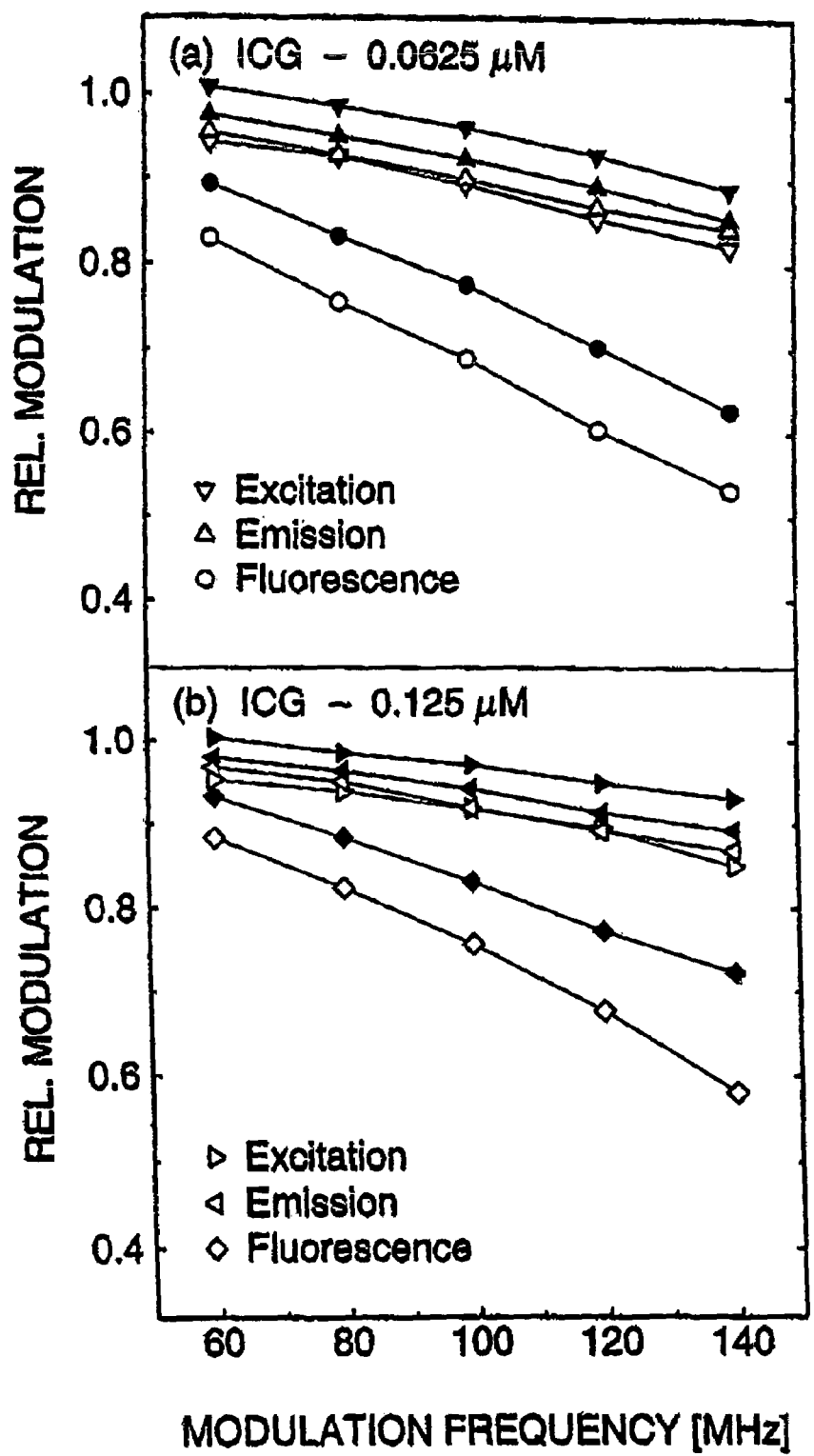
FIG. 9 plots relative modulation attenuation versus modulation frequency for two different concentrations of ICG in a comparative format pertinent to experimental examples.
Figure 10:
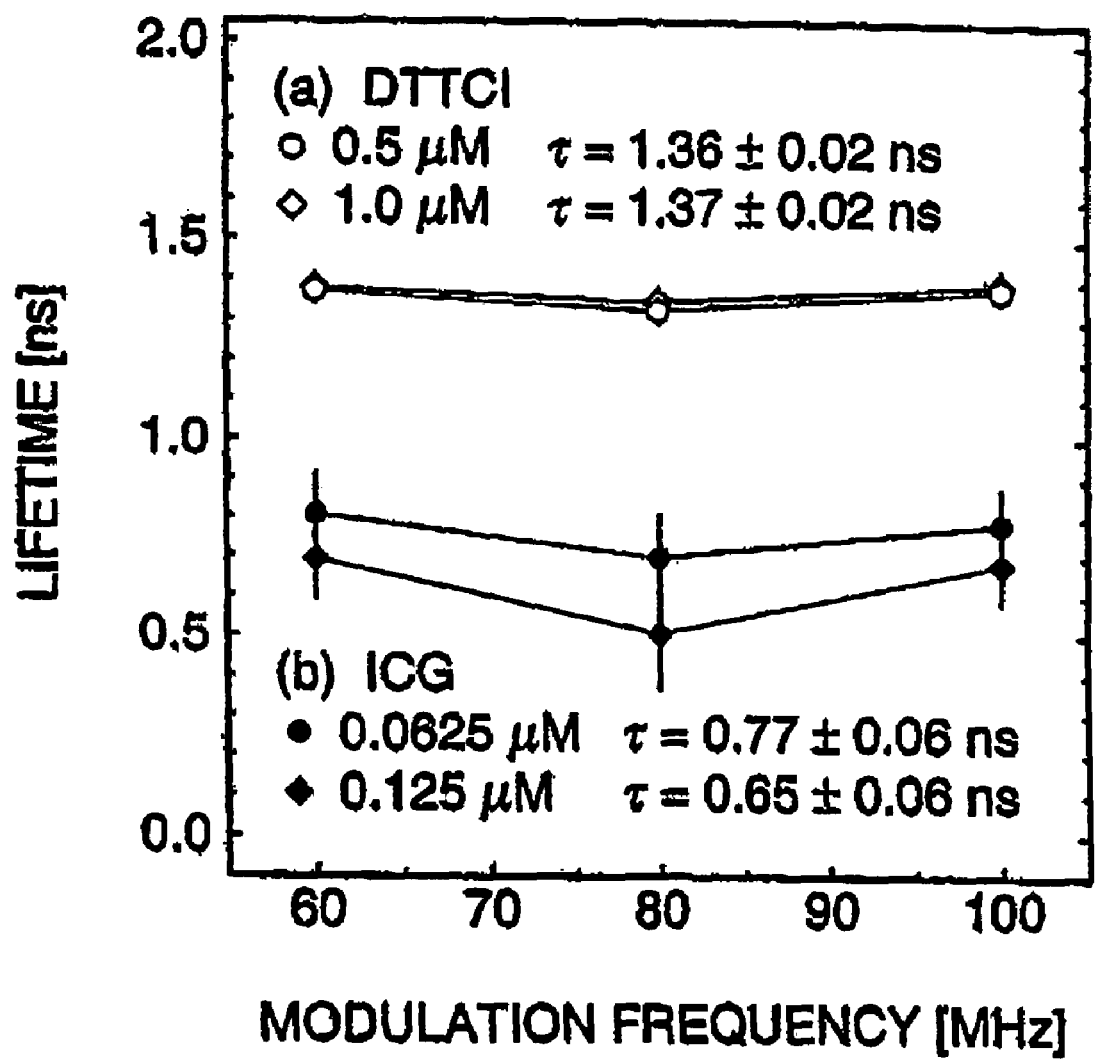
FIG. 10 plots lifetime versus modulation frequency for DTTCI and ICG corresponding to the plots of FIGS. 8 and 9.

Experiments were also conducted determining lifetime based on relative modulation attenuation measurements with detector 48. FIG. 8 provides relative modulation magnitude versus modulation frequency plots of fluorescence, emission, and excitation characterization for the two DTTCI concentrations as illustrated by different curve-fitted symbols. FIG. 9 provides relative modulation magnitude versus modulation frequency plots of fluorescence, emission, and excitation characterizations for the two ICG concentrations as illustrated by different curve-fitted symbols. FIG. 10 provides the lifetime calculations for the two concentrations of DTTCI and ICG based on the measurements plotted in FIGS. 8 and 9.

All publications, patents, and patent applications cited in this specification are herein incorporated by reference as if each individual publication, patent, or patent application were specifically and individually indicated to be incorporated by reference and set forth in its entirety herein. Furthermore, the following are hereby expressly incorporated by reference: U.S. Pat. No. 5,865,754 to Sevick-Muraca et al; U.S. Pat. No. 5,818,583 to Sevick-Muraca et al.; pending U.S. patent application Ser. No. 09/297,895 to Sevick-Muraca et al. filed on 30 Jun. 1999; pending U.S. patent application to Sevick-Muraca et al. entitled "Imaging of Light Scattering Tissues with Fluorescent Contrast Agents" filed 22 Nov. 1999 as a national stage application of International Application Number PCT/US98/02354 (U.S. patent application Ser. No. 09/367,148); and U.S. Provisional Patent Application Ser. No. 60/103,609 to Sevick-Muraca et al. filed on 9 Oct. 1998. While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

What is claimed is:

1. A method, comprising:
    interrogating a light scattering medium including an amount of a selected luminophore with light at an emission wavelength of the luminophore;
    sensing multiply scattered light at the emission light wavelength in response to said interrogating to provide a first optical characterization of the medium;
    exposing the medium to light at an excitation wavelength of the luminophore; and
    detecting a multiply scattered luminescence at the emission wavelength in response to said exposing; and
    illuminating the medium with the excitation light wavelength and detecting multiply scattered light at the excitation wavelength in response to illuminating to establish a second optical characterization of the medium and determining a value corresponding to lifetime of the luminophore from the first optical characterization, the second optical characterization, and the luminescence.

2. The method of claim 1, wherein the first optical characterization corresponds to photon density of the medium with respect to the emission light wavelength.

3. The method of claim 1, wherein the emission light wavelength and the excitation light wavelength are modulated at a predetermined frequency and said sensing and said detecting include determining at least one of a phase difference and a modulation attenuation.

4. The method of claim 1, wherein said exposing is performed with modulated light of the emission light wavelength, said sensing includes detecting the multiply scattered light at each of a number of different frequencies of the modulated light, and the first optical characterization includes determining a number of values by regression with respect to data obtained from said sensing over the different frequencies.

5. The method of claim 1, wherein the first optical characterization includes an absorption coefficient and an isotropic scattering coefficient of the medium at the emission light wavelength.

6. The method of claim 1, wherein the light scattering medium is a living tissue and the luminophore is an exogenous probe introduced into the tissue to perform a medical diagnosis.

7. A method, comprising:
    exposing a light scattering medium including an amount of a luminophore to a number of different light wavelengths selected relative to the luminophore;
    establishing a plurality of optical characteristics of the medium by sensing multiply scattered light at each of the different wavelengths; and
    determining a value corresponding to lifetime of the luminophore from the optical characteristics and a multiply scattered emission at a first one of the light wavelengths caused by exposure of the medium to a second one of the light wavelengths.

8. The method of claim 7, where the first one of the light wavelengths corresponds to an emission wavelength of the luminophore and the second one of the light wavelengths corresponds to an excitation wavelength of the luminophore.

9. The method of claim 7, wherein the optical characteristics correspond to absorption and isotropic scattering coefficients of the medium at each of the different wavelengths.

10. The method of claim 7, wherein the different wavelengths are each modulated over time and said exposing and said establishing are performed for each of a number of different modulation frequencies.

11. The method of claim 7, wherein said establishing includes determining at least one of a phase difference and a modulation attenuation.

12. The method of claim 7, wherein the light scattering medium is a living tissue and the luminophore is an exogenous probe introduced into the tissue to perform a medical diagnosis.

13. A method, comprising:
    evaluating a light scattering medium including an amount of a luminophore with a light interrogation system, the system including a first device optically coupled to a first site of the medium and a second device optically coupled to a second site of the medium spaced apart from the first site;
    subjecting the medium to a first wavelength selected to the luminophore;

optically coupling the first device to the second site and the second device to the first site;

exposing the medium to the first light wavelength after said optically coupling; and detecting a multiply scatteredd luminescence at the emission wavelength, repeating said subjecting, said optically coupling, and said exposing with a second light wavelength in place of the first wavelength, and determining a value corresponding to lifetime of the luminophore from a first and second output of the first wavelength and a first and second output of the second wavelength and the luminescence.

14. The method of claim 5, wherein the first device includes a first light sensor, the second device includes a second light sensor, and the first light wavelength corresponds to at least one of an emission wavelength and an excitation wavelength of the luminophore.

15. The method of claim 13, wherein the first light output and the second light output are each of the first light wavelength.

16. The method of claim 13, wherein the first light wavelength corresponds to an emission wavelength of the luminophore; and said subjecting, said optically coupling, and said exposing are performed to provide a light scattering characterization of the medium at the emission wavelength, the first output light and the second output light being of the first light wavelength.

17. The method of claim 13, wherein the first light wavelength corresponds to an excitation wavelength of the luminophore; and said subjecting, said optically coupling, and said exposing are performed to provide a light scattering characterization of the medium at the excitation wavelength, the first light output and the second light output being of the first light wavelength.

18. The method of claim 17, further comprising repeating said subjecting, said, optically coupling, and said exposing with a second light wavelength in place of the first light wavelength, the second light wavelength corresponding to an emission wavelength of the luminophore to provide a light scattering characterization of the medium at the emission wavelength, the first light output and the second light output being of the second light wavelength.

19. The method of claim 17, further comprising repeating said subjecting, said optically coupling, and said exposing; the first light output and the second light output being of a second light wavelength corresponding to an emission wavelength of the luminophore.

20. The method of claim 13, wherein the first light wavelength corresponds to an excitation wavelength of the luminophore and the first light output and the second light output are of a second light wavelength corresponding to an emission wavelength of the luminophore.

21. The method of claim 13, wherein said subjecting and said exposing are performed with a modulated light source spaced apart from the first site and the second site.

22. The method of claim 13, wherein the first light output and the second light output correspond to at least one of a phase difference and a modulation attenuation.

23. The method of claim 13, further comprising selectively filtering light according to wavelength.

24. The method of claim 1, further comprising introducing the amount of luminophore into the medium.

25. The method of claim 1, wherein the luminophore is a fluorophore.

26. The method of claim 1, wherein said determining is performed in accordance with a relationship corresponding to multiple light scattering behavior of the medium.

27. The method of claim 26, wherein the relationship is based on a diffusion equation model of multiply scattered light in the frequency domain.

28. An apparatus including an light source apparatus, light detection instrumentation, and means for performing the method of claim 1.

29. A system comprising:

light source instrumentation to selectively illuminate a light scattering medium including a luminophore;

detection instrumentation to detect multiply scattered light output from the medium in response to illumination by said light source instrumentation; and a processor operatively coupled to said detection instrumentation to determine a first optical characterization of the medium from a first multiply scattered light output of a first illumination light wavelength and a second optical characterization of the medium from a second multiply scattered light output of a second illumination light wavelength different than said first illumination light wavelength, said processor being operable to calculate a value corresponding to lifetime of the luminophore from the first optical characterization, the second optical characterization, and a multiply scattered emission of the luminophore from the medium in response to excitation.

30. The system of claim 29, further comprising a container to receive the medium, that is optically coupled to said light source instrumentation and said detection instrumentation.

31. The system of claim 29, wherein said light source instrumentation includes a pair of light sources, a first one of the light sources providing light at the first illumination light wavelength and a second one of the light source providing light at the second illumination light wavelength.

32. The system of claim 29, wherein said light source instrumentation is operable to provide modulated light of the first illumination light wavelength and the second illumination wavelength.

33. The system of claim 29, wherein the first illumination light wavelength corresponds to an emission wavelength for the luminophore and the second illumination light wavelength corresponds to an excitation wavelength for the luminophore.

34. The system of claim 29, wherein said detection instrumentation includes a first light sensor optically coupled to a first position in the medium and a second light sensor optically coupled to second position in the medium spaced apart from the first position, said detection instrumentation being reconfigurable to optically couple said first light sensor to said second position and said second light sensor to said first position.

35. The system of claim 34, further comprising a first optical coupler to transmit light from said first position to said first or second sensor, and a second optical coupler to transmit light from said second site to said first or second sensor.

36. The system of claim 29, wherein said processor calculates said value in accordance with a relationship corresponding to multiple light scattering behavior of the medium.

37. The system of claim 36, wherein said relationship is based on a diffusion equation model of multiply scattered light in the frequency domain.

38. The system of claim 29, wherein said detection instrumentation provides one or more output signals to said processor corresponding to at least one of a phase difference and a modulation attenuation.

39. A system, comprising:
means for illuminating a light scattering medium including a luminophore; and
means for characterizing light scattering behavior of the medium for an excitation wavelength of the luminophore and an emission wavelength of the luminophore;
means for determining lifetime of the luminophore from said characterizing means and a multiply scattered light emission from the medium at the emission wavelength in response to illumination by light at the excitation wavelength.

* * * * *